United States Patent
Kimura et al.

(10) Patent No.: US 11,172,897 B2
(45) Date of Patent: Nov. 16, 2021

(54) RADIATION PHASE CONTRAST IMAGING DEVICE

(71) Applicant: Shimadzu Corporation, Kyoto (JP)

(72) Inventors: Kenji Kimura, Kyoto (JP); Taro Shirai, Kyoto (JP); Takahiro Doki, Kyoto (JP); Satoshi Sano, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 145 days.

(21) Appl. No.: 16/643,701

(22) PCT Filed: Oct. 12, 2018

(86) PCT No.: PCT/JP2018/038187
§ 371 (c)(1),
(2) Date: Mar. 2, 2020

(87) PCT Pub. No.: WO2019/130728
PCT Pub. Date: Jul. 4, 2019

(65) Prior Publication Data
US 2020/0205761 A1    Jul. 2, 2020

(30) Foreign Application Priority Data

Dec. 25, 2017 (JP) .............................. JP2017-248336

(51) Int. Cl.
*A61B 6/00* (2006.01)
*G06T 7/00* (2017.01)
*G01N 23/20* (2018.01)

(52) U.S. Cl.
CPC ............ *A61B 6/484* (2013.01); *A61B 6/4291* (2013.01); *A61B 6/5205* (2013.01);
(Continued)

(58) Field of Classification Search
CPC ..... A61B 6/4291; A61B 6/484; A61B 6/5205; A61B 6/5235; A61B 6/54; A61B 6/547;
(Continued)

(56) References Cited

U.S. PATENT DOCUMENTS

2014/0226783 A1* 8/2014 Ning .................. A61B 6/502
378/5
2015/0092916 A1* 4/2015 Baturin ................ A61B 6/461
378/36

(Continued)

FOREIGN PATENT DOCUMENTS

JP    2016-096831 A    5/2016

OTHER PUBLICATIONS

International Search Report with English translation and Written Opinion with Machine translation dated Jan. 15, 2019 in corresponding International Application No. PCT/JP2018/038187; 14 pages.

*Primary Examiner* — Mark R Gaworecki
(74) *Attorney, Agent, or Firm* — Maier & Maier, PLLC

(57) ABSTRACT

A radiation phase contrast imaging device includes an X-ray source, an X-ray detector configured to detect radiated X-rays, a plurality of gratings, an image processor configured to generate a reconstructed image from an X-ray image acquired from the X-ray detector, a display, and a controller configured or programmed to perform control to display, on the display, the X-ray image before reconstruction and the reconstructed image generated by the image processor.

13 Claims, 10 Drawing Sheets

(52) U.S. Cl.
CPC ............. *A61B 6/5235* (2013.01); *A61B 6/54* (2013.01); *A61B 6/584* (2013.01); *G01N 23/20* (2013.01); *G06T 7/0012* (2013.01); *A61B 6/547* (2013.01); *G06T 2207/10116* (2013.01); *G06T 2207/30004* (2013.01)

(58) Field of Classification Search
CPC ...... A61B 6/584; G01N 23/20; G06T 7/0012; G06T 2207/30004
See application file for complete search history.

(56) References Cited

U.S. PATENT DOCUMENTS

| | | | |
|---|---|---|---|
| 2016/0161427 A1* | 6/2016 | Butler | A61B 6/032 250/390.02 |
| 2017/0082559 A1* | 3/2017 | Arboleda | G21K 1/025 |
| 2017/0258423 A1* | 9/2017 | Bartl | A61B 6/4035 |
| 2017/0319149 A1* | 11/2017 | Koehler | A61B 6/484 |

* cited by examiner

FIRST STEP IMAGING

SECOND STEP IMAGING (a)

| 1-B | 1-C | 1-D | 1-E |

RECONSTRUCT (b)

| 1-B | 1-C | 1-D | 1-E | 2-B | 2-C | 2-D | 2-E |

RECONSTRUCT (c)

| 1-B | 1-C | 1-D | 1-E | 2-B | 2-C | 2-D | 2-E | 3-B | 3-C | 3-D | 3-E |

RECONSTRUCT (d)

| 1-B | 1-C | 1-D | 1-E | 2-B | 2-C | 2-D | 2-E | 3-B | 3-C | 3-D | 3-E | 4-B | 4-C | 4-D | 4-E |

RECONSTRUCT (e)

| 1-B | 1-C | 1-D | 1-E | 2-B | 2-C | 2-D | 2-E | 3-B | 3-C | 3-D | 3-E | 4-B | 4-C | 4-D | 4-E | 5-B |

RECONSTRUCT

FIRST STEP IMAGING

SECOND STEP IMAGING (a)

(b)

(c)

RADIATION PHASE CONTRAST IMAGING DEVICE

TECHNICAL FIELD

The present invention relates to a radiation phase contrast imaging device, and more particularly, it relates to the display of an X-ray image of a radiation phase contrast imaging device configured to perform imaging using a plurality of gratings.

BACKGROUND ART

Conventionally, a radiation phase contrast imaging device configured to perform imaging using a plurality of gratings is known. Such a radiation phase contrast imaging device is disclosed in Japanese Patent Laid-Open No. 2016-96831, for example.

Conventional phase contrast imaging devices are configured to perform X-ray imaging with a Talbot interferometer and generate a reconstructed image, as disclosed in Japanese Patent Laid-Open No. 2016-96831. These radiation phase contrast imaging devices can check the internal structure of a subject, which cannot be seen from the outside, without performing an action such as opening the subject or breaking the subject, and thus they are used for non-destructive inspection and medical applications.

In the Talbot interferometer, imaging is performed using a phase grating and an absorption grating. Specifically, a phase contrast image is generated by fringe scanning imaging in which either the phase grating or the absorption grating is translated in a direction orthogonal to the grating pattern, or a moire single shot technique of capturing images by rotating the phase grating or the absorption grating about an X-ray optical axis by a small angle to form a moire fringe, for example. The phase contrast image includes a phase differential image and a dark-field image. The phase differential image is an image formed based on an X-ray phase shift generated when an X-ray passes through the subject. The dark-field image is a visibility image obtained by a change in visibility based on small-angle scattering of an object. Furthermore, the dark-field image is also called a small-angle scattering image. The "visibility" denotes sharpness.

Japanese Patent Laid-Open No. 2016-96831 discloses an X-ray imaging system including an X-ray source, a subject table, a plurality of gratings in which a plurality of slits are arranged in a direction orthogonal to an X-ray irradiation direction, an X-ray detector in which a conversion element configured to accumulate charges and generate an electric signal in accordance with X-rays radiated by the X-ray source and transmitted through a subject and the plurality of gratings is arranged in a two-dimensional manner and a moire fringe image is acquired by reading the electric signal generated by the conversion element as an image signal, and reconstruction means configured to generate a reconstructed image of the subject based on the moire fringe image acquired by the X-ray detector. The reconstruction means is configured to generate a moire fringe image for reconstruction based on a plurality of original moire fringe images acquired by the X-ray detector, and generate the reconstructed image of the subject based on the generated moire fringe image for reconstruction.

PRIOR ART

Patent Document

Patent Document 1: Japanese Patent Laid-Open No. 2016-96831

SUMMARY OF THE INVENTION

Problem to be Solved by the Invention

However, the internal state of the subject cannot be seen from the outside, and in the case of a conventional radiation phase contrast imaging device, the internal state becomes clear only after the reconstructed image (particularly a dark-field image) is generated. Consequently, there is no problem when a portion to be imaged is within the range of an imaging frame, but there is a problem when it is not included in the range of the imaging frame or does not fit within the range of the imaging frame. In this case, a user such as an imaging technician needs to adjust the position of the subject and capture an image again. Consequently, the procedure of acquiring a number of X-ray images, acquiring a reconstructed image based on the images, and checking whether or not the portion to be imaged is within the imaging range is repeated until the reconstructed image desired by the user is acquired, and it takes time to acquire the reconstructed image desired by the user.

The present invention is intended to solve the above problem. The present invention aims to provide a radiation phase contrast imaging device capable of quickly grasping a portion to be imaged, adjusting the position of a subject, and acquiring a desired reconstructed image.

Means for Solving the Problems

In order to attain the aforementioned object, a radiation phase contrast imaging device according to a first aspect of the present invention includes an X-ray source, an X-ray detector configured to detect radiated X-rays, a plurality of gratings including a first grating provided between the X-ray source and the X-ray detector, the first grating through which the X-rays pass, and a second grating irradiated with the X-rays that have passed through the first grating, a moving mechanism configured to move the first or second grating stepwise, an image processor configured to generate a reconstructed image from an X-ray image acquired from the X-ray detector, a display, and a controller configured or programmed to perform control to display, on the display, the X-ray image before reconstruction and the reconstructed image generated by the image processor.

As described above, the radiation phase contrast imaging device according to the first aspect of the present invention includes the controller configured or programmed to perform control to display, on the display, the X-ray image before reconstruction and the reconstructed image generated by the image processor 6. Accordingly, the X-ray image before reconstruction can be displayed on the display in advance before the reconstructed image is generated. Consequently, a user can know the approximate position of a portion to be imaged from the X-ray image before reconstruction displayed on the display and can adjust the position of a subject without waiting for generation of the reconstructed image. Thus, a desired reconstructed image can be acquired without recapturing the X-ray image before reconstruction many times. Consequently, it is possible to quickly grasp the portion to be imaged, adjust the position of the subject, and acquire the desired reconstructed image.

In the aforementioned radiation phase contrast imaging device according to the first aspect, the controller is preferably configured or programmed to perform control to display the X-ray image before reconstruction on the display every time one or plurality of X-ray images are acquired from the X-ray detector, and to control the image processor to generate the reconstructed image and display the reconstructed image that has been generated on the display. Accordingly, every time the X-ray image before reconstruction is acquired, the X-ray image before reconstruction displayed on the display is updated. Consequently, the user can grasp the approximate position of the portion to be imaged by confirming the updated X-ray image before reconstruction, and can adjust the position of the subject as soon as possible. Furthermore, control is performed to update the X-ray image before reconstruction displayed on the display every time a plurality of X-ray images before reconstruction are acquired such that the plurality of X-ray images before reconstruction can be overlaid, and thus a clear X-ray image before reconstruction can be displayed.

In the aforementioned radiation phase contrast imaging device according to the first aspect, the controller is preferably configured or programmed to perform control to display the X-ray image before reconstruction and the reconstructed image side by side on the display. Accordingly, the user can easily grasp where the portion to be imaged is in the imaging range by comparing the X-ray image before reconstruction with the reconstructed image. When the portion to be imaged is deviated from a desired position, the position of the portion to be imaged can be quickly adjusted.

In the aforementioned radiation phase contrast imaging device according to the first aspect, the reconstructed image preferably includes an absorption image, a dark-field image, and a phase differential image. Accordingly, the user can confirm the approximate position of the portion to be imaged using the X-ray image before reconstruction. In addition, it is possible to specify the more accurate position of the portion to be imaged using the absorption image, the dark-field image, and the phase differential image after reconstruction. Consequently, the position of the portion to be imaged can be quickly adjusted when the portion to be imaged is deviated from the desired position.

In the aforementioned radiation phase contrast imaging device according to the first aspect, an update period of the X-ray image before reconstruction is preferably shorter than an update period of the reconstructed image. Accordingly, the X-ray image before reconstruction is displayed on the display in a short time. Consequently, the user can adjust the imaging position in a short time.

In the aforementioned radiation phase contrast imaging device according to the first aspect, the radiation phase contrast imaging device is preferably configured to operate in a high-speed imaging mode in which the X-ray image is captured with a shorter X-ray charge accumulation time in the X-ray detector than that in a standard imaging mode, and the reconstructed image generated using the X-ray image that has been acquired is displayed on the display. Accordingly, in the high-speed imaging mode, the time required to acquire X-ray images used for reconstruction can be reduced as compared with the conventional art, and the time required to generate and display the reconstructed image can be reduced. Consequently, the position of the portion to be imaged can be quickly grasped, and the position of the subject can be adjusted.

A radiation phase contrast imaging device according to a second aspect of the present invention includes an image processor configured to generate a reconstructed image from an X-ray image before reconstruction acquired from an X-ray detector, a display, and a controller configured or programmed to perform control to display, on the display, the X-ray image before reconstruction and the reconstructed image generated by the image processor, and the radiation phase contrast imaging device is configured to operate in a high-speed imaging mode in which the X-ray image is captured with a shorter X-ray charge accumulation time in the X-ray detector than that in a standard imaging mode, and the reconstructed image generated using the X-ray image that has been acquired is displayed on the display. Accordingly, the time required to acquire X-ray images necessary for reconstruction can be reduced as compared with the conventional art, and the time required to acquire and display the reconstructed image can be reduced. Thus, a user can quickly grasp a portion to be imaged from the displayed reconstructed image. In addition, the user can quickly adjust the position of a subject and acquire a desired reconstructed image.

In the aforementioned radiation phase contrast imaging device according to the second aspect, the image processor is preferably configured to, in the high-speed imaging mode, generate the reconstructed image using a plurality of acquired X-ray images after first fringe scanning imaging is completed, and generate, in second and subsequent fringe scanning imaging, the reconstructed image using a plurality of X-ray images acquired in previous fringe scanning imaging and a plurality of X-ray images acquired in new fringe scanning imaging. Accordingly, even when the image quality of X-ray images acquired by one fringe scanning imaging operation is rough (a lot of noise), a clearer (less noise) reconstructed image can be acquired as the number of used images is increased by performing the fringe scanning imaging a larger number of times. Consequently, even when X-ray images with a lot of noise captured with a shorter X-ray charge accumulation time in the X-ray detector than that in the standard imaging mode are used, a clearer image can be obtained as the number of times of fringe scanning imaging is increased, and the portion to be imaged can be quickly grasped. Furthermore, the position of the subject can be adjusted, and a desired reconstructed image can be acquired. The fringe scanning imaging means that one of the first grating and the second grating is moved n times at equal intervals in a direction perpendicular to grooves of the grating, the grating is stopped every time it is moved once, and a plurality of X-ray images are repeatedly captured n times. Furthermore, 1/n times of imaging are referred to as a step.

In this case, the image processor is preferably configured to generate the reconstructed image using the X-ray images acquired by a predetermined number of most recent fringe scanning imaging operations in the high-speed imaging mode. Accordingly, as compared with the case in which all the X-ray images acquired by the fringe scanning imaging are used, the number of images used for reconstruction can be reduced, and the time required for reconstruction can be reduced. In addition, it is not necessary to use images captured before the predetermined number, and thus it is possible to avoid an afterimage remaining when the position of the subject is moved.

In this case, the image processor is preferably configured to generate the reconstructed image using the plurality of X-ray images previously acquired every time one step imaging is completed from predetermined fringe scanning imaging in the high-speed imaging mode. Accordingly, the reconstructed image can be generated and displayed on the display at an even shorter interval than when update is performed every fringe scanning imaging. Consequently, adjustment of the position of the subject can be reflected in the reconstructed image more quickly.

In the aforementioned radiation phase contrast imaging device according to the second aspect, the moving mechanism is preferably configured to switch a direction of step movement to an opposite direction every time fringe scanning imaging is completed. Accordingly, the radiation phase contrast imaging device can move to the next fringe scanning imaging in a short time, and the time required to return the position of the grating to the initial position can be reduced. The step movement means that the grating moves in the direction perpendicular to the grooves of the grating.

In the aforementioned radiation phase contrast imaging device according to the second aspect, the reconstructed image preferably includes an absorption image, a dark-field image, and a phase differential image. Accordingly, the user can confirm the position of the portion to be imaged using the absorption image, the dark-field image, and the phase differential image after reconstruction.

In the radiation phase contrast imaging device according to the second aspect of the present invention, the radiation phase contrast imaging device is preferably further configured to operate in the standard imaging mode in which the X-ray image is captured with a longer X-ray charge accumulation time in the X-ray detector than that in the high-speed imaging mode, and the reconstructed image generated using the X-ray image that has been acquired is displayed on the display, and the controller is preferably configured or programmed to, in the high-speed imaging mode, control the image processor to perform at least one of following A to C operations: A: to reduce a number of step movements of fringe scanning imaging as compared with the standard imaging mode, B: to reduce a number of captured images per step as compared with the standard imaging mode, and C: to reduce an exposure time per X-ray image as compared with the standard imaging mode. Accordingly, the time required to acquire X-ray images necessary for reconstruction can be shorter than that in the standard imaging mode. Thus, the time required to acquire and display the reconstructed image can be reduced.

Effect of the Invention

According to the present invention, as described above, it is possible to quickly grasp the portion to be imaged, adjusting the position of the subject, and acquiring a desired reconstructed image.

BRIEF DESCRIPTION OF THE DRAWINGS

FIG. 7 is a diagram showing the timing of reconstructed image generation in the high-speed imaging mode according to the second embodiment of the present invention.

MODES FOR CARRYING OUT THE INVENTION

Embodiments embodying the present invention are hereinafter described on the basis of the drawings.

First Embodiment

The configuration of a radiation phase contrast imaging device 100 according to a first embodiment of the present invention, and a method for displaying a reconstructed image 11 and an X-ray image 10 before reconstruction on a display 7 according to the first embodiment of the present invention are described with reference to FIGS. 1 to 3.

(Configuration of Radiation Phase Contrast Imaging Device)

The configuration of the radiation phase contrast imaging device 100 according to the first embodiment of the present invention is now described with reference to FIGS. 1 and 2.

Figure 1:
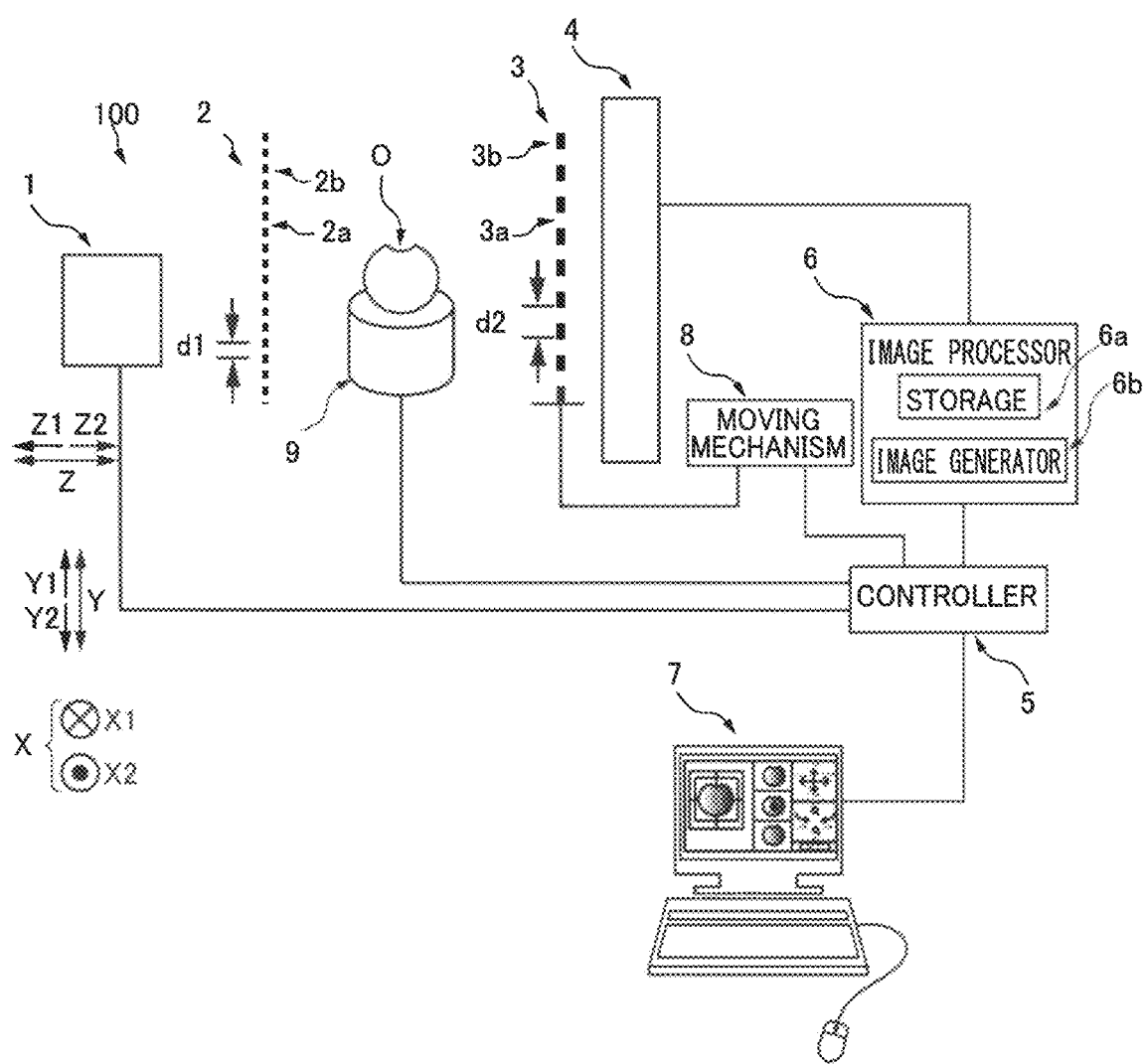
FIG. 1 is a schematic view showing a radiation phase contrast imaging device according to a first embodiment of the present invention, as viewed in an X direction.

FIG. 1 is a diagram showing the radiation phase contrast imaging device 100, as viewed in an X direction. As shown in FIG. 1, the radiation phase contrast imaging device 100 includes an X-ray source 1, a first grating 2, a second grating 3, an X-ray detector 4, a controller 5, an image processor 6, the display 7, a moving mechanism 8, and a stage 9. In this specification, a direction from the X-ray source 1 toward the first grating 2 is defined as a Z2 direction, and the opposite direction is defined as a Z1 direction. The Z2 direction and the Z1 direction are collectively referred to as a Z direction. Furthermore, a left-right direction in a plane orthogonal to the Z direction is defined as the X direction, a direction toward the rear side of the plane of the figure is defined as an X2 direction, and a direction toward the front side of the plane of the figure is defined as an X1 direction. Furthermore, an upward-downward direction in the plane orthogonal to the Z direction is defined as a Y direction, an upward direction is defined as a Y1 direction, and a downward direction is defined as a Y2 direction.

The X-ray source 1 is configured to generate X-rays when a high voltage is applied thereto based on a signal from the controller 5 and radiate the generated X-rays toward the X-ray detector 4 (in the Z2 direction).

Between the X-ray source 1 and the X-ray detector 4, there are a plurality of gratings including the first grating 2 through which the X-rays pass and the second grating 3 irradiated with the X-rays that have passed through the first grating 2. The first grating 2 includes a plurality of slits 2a and X-ray phase changers 2b arranged in the Y direction at a predetermined period (pitch) d1. The slits 2a and the X-ray phase changers 2b are each formed so as to extend linearly. Furthermore, the slits 2a and the X-ray phase changers 2b are each formed so as to extend in parallel. The first grating 2 is a so-called phase grating.

The first grating 2 is arranged between the X-ray source 1 and the second grating 3, and the X-rays are radiated thereto from the X-ray source 1. The first grating 2 forms a self-image (not shown) of the first grating 2 by a Talbot effect. When X-rays with coherence pass through a grating in which slits are formed, an image (self-image) of the grating is formed at a position away from the grating by a predetermined distance (Talbot distance). This is called a Talbot effect.

The second grating 3 includes a plurality of X-ray transmitters 3a and X-ray absorbers 3b arranged in the Y direction at a predetermined period (pitch) d2. The X-ray transmitters 3a and the X-ray absorbers 3b are each formed so as to extend linearly. Furthermore, the X-ray transmitters 3a and the X-ray absorbers 3b are each formed so as to extend in parallel. The second grating 3 is a so-called absorption grating. The first grating 2 and the second grating 3 are gratings having different roles, but the slits 2a and the X-ray transmitters 3a transmit X-rays. Furthermore, the X-ray absorbers 3b play a role of shielding X-rays, and the X-ray phase changers 2b change the phase of X-rays by a refractive index difference with the slits 2a.

The second grating 3 is arranged between the first grating 2 and the X-ray detector 4, and the X-rays that have passed through the first grating 2 are radiated thereto. Furthermore, the second grating 3 is arranged at a position away from the first grating 2 by the Talbot distance. The second grating 3 interferes with the self-image of the first grating 2 to form a moire fringe (not shown) on a detection surface of the X-ray detector 4. That is, the radiation phase contrast imaging device 100 includes the first grating 2 and the second grating 3 as the plurality of gratings, and in the Z2 direction from the X-ray source 1 toward the X-ray detector 4, the first grating 2 and the second grating 3 are arranged in this order.

The X-ray detector 4 is configured to detect X-rays, convert the detected X-rays into electric signals, and read the converted electric signals as image signals. The X-ray detector 4 is a flat panel detector (FPD), for example. The X-ray detector 4 includes a plurality of conversion elements (not shown) and pixel electrodes (not shown) arranged on the plurality of conversion elements. The plurality of conversion elements and pixel electrodes are arranged in an array manner in the X direction and Y direction at a predetermined period (pixel pitch). Furthermore, the X-ray detector 4 is configured to output the acquired image signals to the image processor 6.

The controller 5 controls the image processor 6 to generate the reconstructed image 11 based on the image signals output from the X-ray detector 4 to the image processor 6. The controller 5 controls the moving mechanism 8 to move the second grating 3 stepwise in a direction orthogonal to a grating direction in a grating plane. The controller 5 includes a processor such as a central processing unit (CPU). Note that the grating direction refers to a direction in which the slits 2a, the X-ray phase changers 2b, the X-ray transmitters 3a, the X-ray absorbers 3b, etc. extend, and is the X direction in an example shown in FIG. 1. In the example shown in FIG. 1, a direction orthogonal to the grating direction is the Y direction. The controller 5 also performs control to display, on the display 7, the reconstructed image 11 generated by the image processor 6 and the X-ray image 10 before reconstruction.

The image processor 6 includes a storage 6a configured to accumulate a plurality of frames of image signals output from the X-ray detector 4, and an image generator 6b configured to generate X-ray images based on the image signals accumulated in the storage 6a. The generated X-ray images may be displayed on the display 7 without any change. Furthermore, the generated X-ray images may be displayed on the display 7 after being subjected to correction (image processing) such as adding color and brightness contrast or erasing minute defects by the image processor 6. The X-ray image 10 before reconstruction is a moire fringe image, and is an image in which a moire pattern due to interference overlaps an absorption image 11a after reconstruction. Image processing for removing the moire pattern of the X-ray image 10 before reconstruction may be performed, and an image close to the absorption image 11a after reconstruction may be generated and displayed. In addition, the image processor 6 (image generator 6b) reconstructs a plurality of X-ray images acquired while the second grating 3 is moved stepwise in the direction orthogonal to the grating direction in the grating plane, and generates the reconstructed image 11 (see FIG. 2). Specifically, a plurality of images acquired with the same position of the second grating 3 are added or averaged, one moire fringe image for each position of the second grating 3 (step position for fringe scanning imaging) is generated, and calculation is performed using the principle of a fringe scanning method from the moire fringe images for multiple positions of the second grating 3 (step positions of fringe scanning imaging). The generated reconstructed image 11 includes the absorption image 11a, a dark-field image 11b, and a phase differential image 11c, for example. The absorption image 11a represents the amount of X-rays transmitted through a subject O. The dark-field image 11b represents the amount of small-angle scattering of X-rays at the subject O. The phase differential image 11c represents an X-ray phase change. The image processor 6 (image generator 6b) may generate a plurality of reconstructed images 11, and may generate only the dark-field image 11b in which a crack C (defective portion) can be clearly imaged, for example. The controller 5 performs control to display the generated reconstructed image 11 on the display 7.

The display 7 is a monitor connected to a computer. The display 7 displays the X-ray image 10 before reconstruction and the reconstructed image 11, as shown in FIG. 2. The X-ray image 10 before reconstruction may be displayed on the display 7 every time the image processor 6 acquires the X-ray image 10 before reconstruction from the X-ray detector 4, or may be displayed on the display 7 after a plurality of X-ray images are acquired. The user sets the way of display in the controller 5.

The display 7 displays a region 12 in which a grating can be imaged and a central region 13 of the region 12 in which a grating can be imaged. The subject O is only required to be included in the region 12 in which a grating can be imaged, but the subject O is preferably included in the central region 13. The subject O is included in the central region 13 such that the image processor 6 can trim an extra portion of the region 12 in which a grating can be imaged, and use only the X-ray image in the central region 13 to reconstruct the reconstructed image 11. In addition, the size of the X-ray image used for reconstruction and the amount of calculation for reconstruction can be reduced, and the time of generation of the reconstructed image 11 in the image processor 6 (image generator 6b) can be reduced. When the X-ray image is trimmed, the user may press a trimming button provided on the display 7 such that the imager processor 6 performs trimming. In this case, the trimming button may be provided in such a manner that the user trims the image to an arbitrary area (size). Of the X-ray images captured by irradiating the subject O with X-rays, an image displayed on the display 7 without being reconstructed is defined as the X-ray image 10 before reconstruction, and an image used to generate the reconstructed image 11 is simply defined as the X-ray image. However, this description is for convenience to facilitate understanding of the present invention, and the reconstructed image 11 may be generated using the X-ray image 10 before reconstruction.

Figure 2:
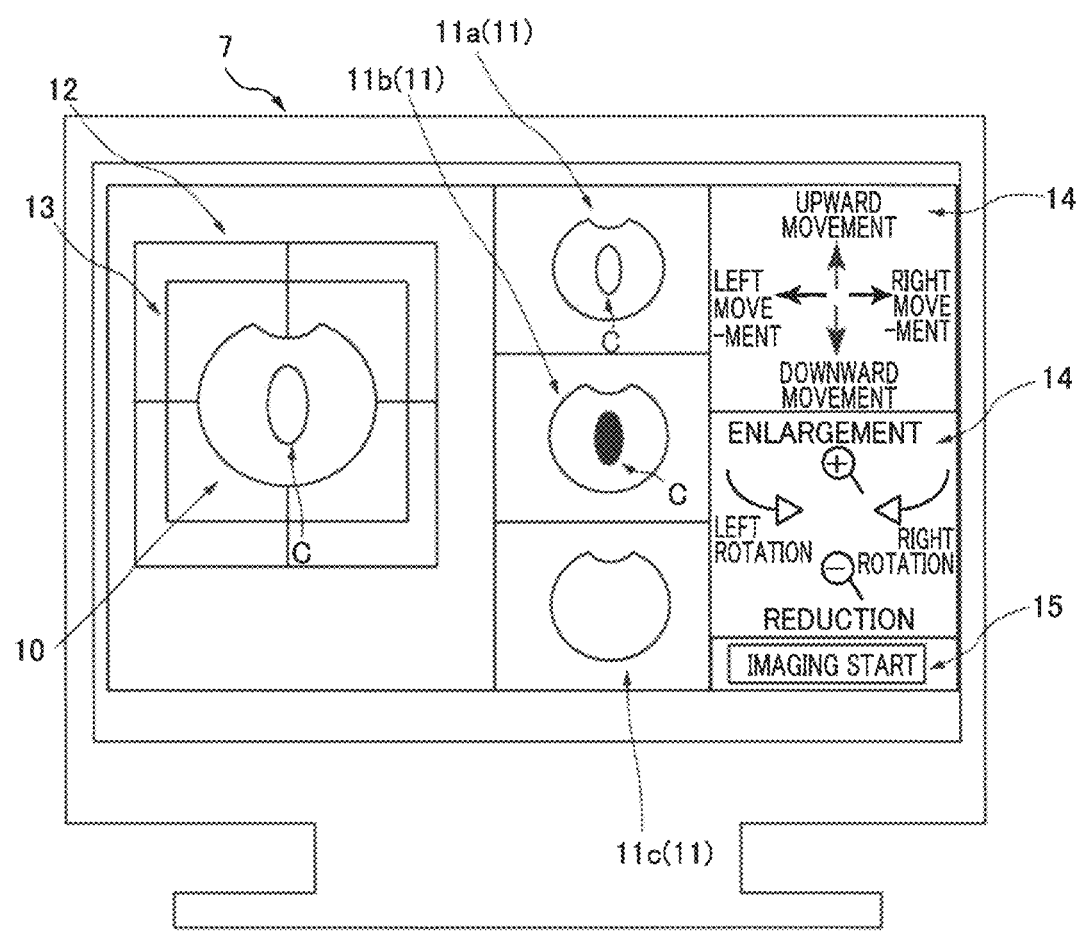
FIG. 2 is a diagram showing an example of images displayed on a display according to the first embodiment of the present invention.
Figure 3:
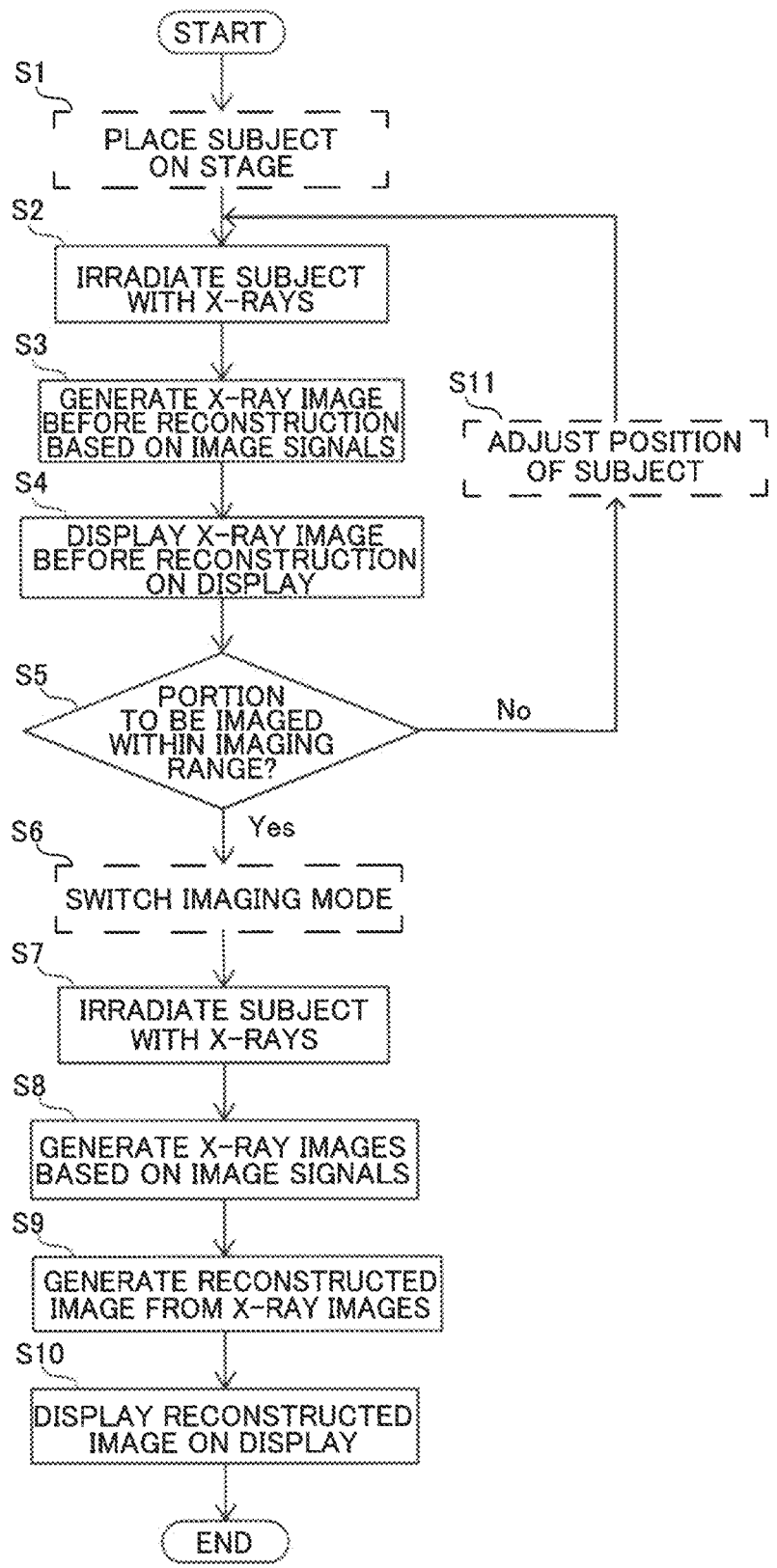
FIG. 3 is a diagram showing the operation of the radiation phase contrast imaging device according to the first embodiment of the present invention.

The display 7 may display the X-ray image 10 before reconstruction and the reconstructed image 11 side by side (see FIG. 2). The images are displayed side by side such that the user can compare the X-ray image 10 before reconstruction with the reconstructed image 11 and can confirm a portion to be imaged. Alternatively, either the X-ray image 10 before reconstruction or the reconstructed image 11 may be displayed on the display 7 by switching.

The display 7 displays operation panels 14 for operating the stage 9. The operation panels 14 are operated by clicking with a mouse, for example. The operation panels 14 on the display 7 are operated such that the stage 9 moves or rotates. An upward movement or downward movement key is clicked such that the stage 9 moves in the Y1 or Y2 direction, and a left movement or right movement key is clicked such that the stage 9 moves in the X1 or X2 direction. In addition, an enlargement or reduction key is clicked such that the stage 9 moves in the Z1 or Z2 direction. A left rotation or right rotation key is clicked such that the stage 9 rotates about a Y axis as a rotation axis. Thus, the user can adjust the position of the subject O by adjusting the position and orientation of the stage 9 while checking the X-ray image 10 before reconstruction displayed on the display 7.

The moving mechanism 8 is configured to move the second grating 3 stepwise in the direction (Y direction) orthogonal to the grating direction in the grating plane (in an XY plane) based on a signal from the controller 5. Specifically, the moving mechanism 8 divides the period d2 of the second grating 3 into n, and moves the second grating 3 stepwise by d2/n. Note that n is a positive integer. In the first embodiment, n is equal to 4, for example. The moving mechanism 8 includes a stepping motor or a piezo actuator, for example. Note that the controller 5 may be configured or programmed to move the first grating 2 stepwise in the direction (Y direction) orthogonal to the grating direction in the grating plane (in the XY plane) instead of the second grating 3. In this case, the moving mechanism 8 divides the period d1 of the first grating 2 into n, and moves the first grating 2 stepwise by d1/n.

Although not shown, the stage 9 includes a placement table on which the subject O is placed, a stage driving mechanism, and a stage rotating mechanism. When the user operates the operation panels 14 signals are sent from the controller 5 to the stage driving mechanism or the stage rotating mechanism. When the upward or downward movement key of the operation panel 14 is operated, the controller 5 controls the stage driving mechanism to move the stage 9 in the Y1 direction or the Y2 direction. When the left movement or right movement key of the operation panel 14 is operated, the controller 5 controls the stage driving mechanism to move the stage 9 in the X1 direction or the X2 direction. When the enlargement or reduction key of the operation panel 14 is operated, the controller 5 controls the stage driving mechanism to move the stage 9 in the Z1 direction or the Z2 direction. When the left rotation or right rotation key of the operation panel 14 is operated, the controller 5 controls the stage rotating mechanism to rotate the stage 9 clockwise or counterclockwise about the Y axis as a rotation axis.

The operation of the radiation phase contrast imaging device 100 according to the first embodiment of the present invention is now described with reference to FIG. 3. An example is described in which the radiation phase contrast imaging device 100 is used for non-destructive inspection and the reconstructed image 11 of the crack C that is a portion to be imaged is generated. In step S1, the user first places the subject O to be imaged on the stage 9. Then, the user operates the radiation phase contrast imaging device 100 such that the operation of the radiation phase contrast imaging device 100 moves to step S2. In step S2, the controller 5 controls the X-ray source 1 to irradiate the subject O with X-rays. The operation of the radiation phase contrast imaging device 100 moves to step S3, and the image processor 6 (image generator 6b) generates the X-ray image 10 before reconstruction based on the image signals accumulated in the storage 6a. The operation of the radiation phase contrast imaging device 100 moves to step S4, and the controller 5 controls the image processor 6 to display the X-ray image 10 before reconstruction on the display 7. The operation of the radiation phase contrast imaging device 100 moves to step S5, and the user confirms whether or not the crack C is within the imaging range while viewing the X-ray image 10 before reconstruction displayed on the display 7.

When the crack C (defective portion) is within the imaging range, the operation of the radiation phase contrast imaging device 100 moves to step S6, and the user operates an imaging start button 15 displayed on the display 7. Thus, the operation of the radiation phase contrast imaging device 100 moves to step S7, and the controller 5 controls the X-ray source 1 to irradiate the subject O with X-rays. In step S7, the conditions of the X-ray source 1 may be changed from those in step S2. The operation of the radiation phase contrast imaging device 100 moves to step S8, the image processor 6 (image generator 6b) generates the X-ray images based on the image signals accumulated in the storage 6a. The operation of the radiation phase contrast imaging device 100 moves to step S9, and the controller 5 controls the image processor 6 to reconstruct the generated X-ray images and generate the reconstructed image 11. Then, the operation of the radiation phase contrast imaging device 100 moves to step S10, and the controller 5 controls the image processor 6 to display the reconstructed image 11 on the display 7.

In step S5, when the crack C (defective portion) is outside the imaging range, the operation of the radiation phase contrast imaging device 100 moves to step S11. In step S11, the user adjusts the position of the subject O by moving or rotating the stage 9 such that the crack C (defective portion) is included in the imaging range. Then, the user operates the radiation phase contrast imaging device 100 such that the operation of the radiation phase contrast imaging device 100 returns to step S2.

In the radiation phase contrast imaging device 100 according to the first embodiment of the present invention, an imaging mode differs between when the X-ray image 10 before reconstruction is captured and when the X-ray image for reconstruction is captured. When the user presses the imaging start button 15 displayed on the display 7, the controller 5 switches between a mode in which the X-ray image 10 before reconstruction is captured and a mode in which an X-ray image for generating the reconstructed image 11 is captured. In the mode in which the X-ray image 10 before reconstruction is captured, the controller 5 controls the image processor 6 (image generator 6b) to display the X-ray image 10 before reconstruction on the display 7 without reconstructing the X-ray image 10 before reconstruction every time one or a plurality of X-ray images 10 before reconstruction are captured. In the mode in which the X-ray image for generating the reconstructed image 11 is captured, the controller 5 controls the image processor 6 (image generator 6b) to reconstruct the acquired X-ray images and generate the reconstructed image 11. Furthermore, the controller 5 controls the image processor 6 to display the reconstructed image 11 on the display 7. The image processor 6 may be controlled to display the X-ray image 10 before reconstruction on the display 7 without reconstructing the X-ray image 10 before reconstruction every time one or a plurality of X-ray images 10 before reconstruction are captured, while simultaneously displaying the reconstructed image 11 on the display 7.

The radiation phase contrast imaging device 100 according to the first embodiment of the present invention captures the X-ray image 10 before reconstruction in a shorter time than the X-ray image for reconstruction. Although noise increases when imaging is performed in a short time, the user can grasp the approximate position of the crack C (defective portion) by looking at the X-ray image 10 before reconstruction. Imaging can be performed in a short time such that a display update period of the X-ray image 10 before reconstruction can be shorter than a display update period of the reconstructed image 11. For example, when the radiation phase contrast imaging device 100 captures the X-ray image 10 before reconstruction, the radiation phase contrast imaging device 100 may capture the image with an update period of 100 msec and display it on the display 7. Then, the mode may be switched, and the radiation phase contrast imaging device 100 may capture the reconstructed image 11 with an update period of 400 msec, perform reconstruction with the image processor 6, and then display the reconstructed image 11 on the display 7.

The radiation phase contrast imaging device 100 according to the first embodiment of the present invention is configured to operate in a high-speed imaging mode in order to quickly generate the reconstructed image 11. In the high-speed imaging mode, an X-ray image is captured with a shorter X-ray charge accumulation time in the X-ray detector 4 than that in a standard imaging mode, and the image processor 6 (image generator 6b) is controlled to generate the reconstructed image 11 from the acquired X-ray image. The charge accumulation time refers to a time from when a light receiving element of the X-ray detector 4 receives X-rays until the light receiving element converts the X-rays into image signals.

Advantages of First Embodiment

In the first embodiment, the following advantages are obtained.

In the first embodiment of the present invention, the radiation phase contrast imaging device 100 includes the controller 5 configured or programmed to perform control to display, on the display 7, the X-ray image 10 before reconstruction and the reconstructed image 11 generated by the image processor 6 (image generator 6b), as described above. Accordingly, the X-ray image 10 before reconstruction can be displayed on the display 7 in advance before the reconstructed image 11 is generated. Consequently, the user can know the approximate position of the portion to be imaged from the X-ray image 10 before reconstruction displayed on the display 7 and can adjust the position of the subject O without waiting for generation of the reconstructed image 11. Thus, a desired reconstructed image 11 can be acquired without recapturing the X-ray image 10 before reconstruction many times. Consequently, it is possible to quickly grasp the portion to be imaged, adjust the position of the subject O, and acquire the desired reconstructed image 11.

Furthermore, the controller 5 is configured or programmed to perform control to display the X-ray image 10 before reconstruction on the display 7 every time one or a plurality of X-ray images 10 before reconstruction are acquired from the X-ray detector 4, and to control the image processor 6 (image generator 6b) to generate the reconstructed image 11 and display the reconstructed image 11 that has been generated on the display 7. Accordingly, every time the X-ray image 10 before reconstruction is acquired, the X-ray image 10 before reconstruction displayed on the display 7 is updated. Consequently, the user can grasp the approximate position of the portion to be imaged by confirming the updated X-ray image 10 before reconstruction, and can adjust the position of the subject O as soon as possible. Furthermore, control is performed to update the X-ray image 10 before reconstruction displayed on the display 7 every time a plurality of X-ray images 10 before reconstruction are acquired such that the plurality of X-ray images 10 before reconstruction can be overlaid, and thus a clear X-ray image 10 before reconstruction can be displayed.

Furthermore, the controller 5 is configured or programmed to perform control to display the X-ray image 10 before reconstruction and the reconstructed image 11 side by side on the display 7. Accordingly, the user can easily grasp where the portion to be imaged is in the imaging range by comparing the X-ray image 10 before reconstruction with the reconstructed image 11. When the portion to be imaged is deviated from a desired position, the position of the portion to be imaged can be quickly adjusted.

Furthermore, the X-ray image 10 before reconstruction may be a moire image, image processing for removing the moire pattern may be performed, and an image close to the absorption image 11a may be generated and displayed. The reconstructed image 11 includes the absorption image 11a, the dark-field image 11b, and the phase differential image 11c. Accordingly, the user can confirm the approximate position of the portion to be imaged using the X-ray image 10 before reconstruction. In addition, it is possible to specify the more accurate position of the crack C (defective portion) using the absorption image 11a, the dark-field image 11b, and the phase differential image 11c after reconstruction. Consequently, the position of the portion to be imaged can be quickly adjusted when the portion to be imaged is deviated from the desired position.

Furthermore, the update period of the X-ray image 10 before reconstruction is shorter than the update period of the reconstructed image 11. Accordingly, the X-ray image 10 before reconstruction is displayed on the display 7 in a short time. Consequently, the user can adjust the imaging position in a short time.

Furthermore, the radiation phase contrast imaging device 100 is configured to operate in the high-speed imaging mode in which X-ray images are captured with a shorter X-ray charge accumulation time in the X-ray detector 4 than that in the standard imaging mode, and the reconstructed image 11 generated using the acquired X-ray images is displayed on the display 7. Accordingly, in the high-speed imaging mode, the time required to acquire X-ray images used for reconstruction can be reduced as compared with the conventional art, and the time required to generate the reconstructed image 11 and display the reconstructed image 11 on the display 7 can be reduced. Consequently, the position of the portion to be imaged can be quickly grasped, and the position of the subject O can be adjusted.

Second Embodiment

The operation of a radiation phase contrast imaging device 100 according to a second embodiment of the present invention is now described with reference to FIGS. 4 to 7. Description of the same configuration of the radiation phase contrast imaging device 100 as those of the first embodiment is omitted. In the second embodiment of the present invention, an example is described in which the radiation phase contrast imaging device 100 is used for non-destructive inspection, and a reconstructed image 11 of a crack C (defective portion) that is a portion to be imaged is generated. The case in which a single fringe scanning imaging operation includes four steps is described below.

Figure 4:
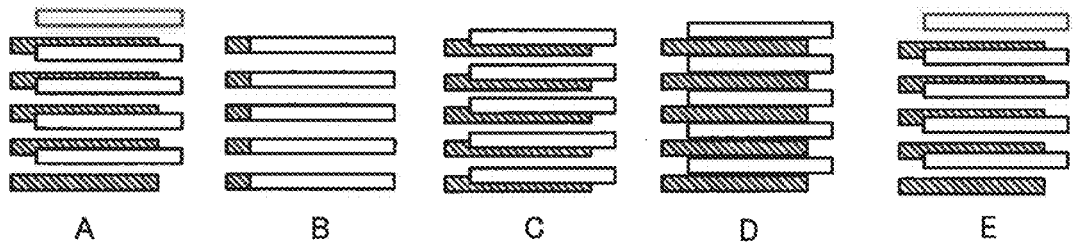
FIG. 4 is a diagram showing grating movement in fringe scanning imaging according to the first embodiment of the present invention.
Figure 4:
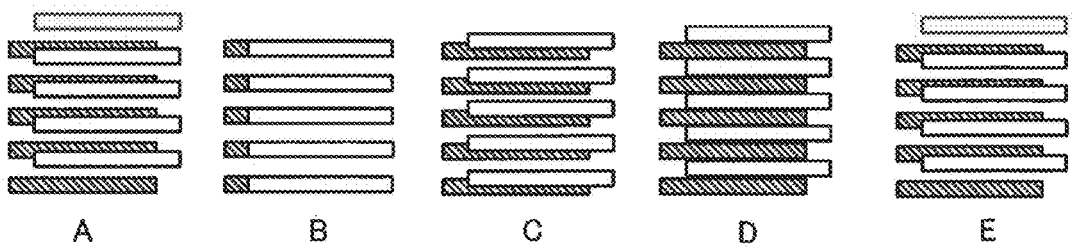

In the second embodiment of the present invention, the radiation phase contrast imaging device 100 is configured to acquire an image of a subject O by fringe scanning imaging. Movement of a grating in the case in which the grating moves four times at equal intervals in a single fringe scanning imaging operation is described with reference to FIG. 4. FIG. 4 shows the positional relationship between a second grating 3 and a self-image as viewed in a Z2 direction when the second grating 3 is imaged at a predetermined pitch in an X direction. A shaded rectangle represents the self-image and a white rectangle represents the second grating 3. In first movement, a moving mechanism 8 moves the second grating 3 to a first step position and arranges the second grating 3 like B. Note that at an initial predetermined step position, the position of the self-image does not need to coincide with the position of the second grating 3. When the second grating 3 is at the initial predetermined step position, it is not necessary to move it. In a state in which the grating is arranged like B, a controller 5 images the subject O and controls a storage 6a to accumulate image signals output from an X-ray detector 4. In second movement, the moving mechanism 8 further moves the grating by ¼, and arranges the second grating 3 like C. In a state in which the grating is arranged like C, the controller 5 images the subject O and controls the storage 6a to accumulate image signals output from the X-ray detector 4. In third movement, the moving mechanism 8 further moves the grating by ¼, and arranges the second grating 3 like D. In a state in which the grating is arranged like D, the controller 5 images the subject O and controls the storage 6a to accumulate image signals output from the X-ray detector 4. In fourth movement, the moving mechanism 8 further moves the grating by ¼, and arranges the second grating 3 like E. In a state in which the grating is arranged like E, the controller 5 images the subject O and controls the storage 6a to accumulate image signals output from the X-ray detector 4. Thus, first fringe scanning imaging is completed. When the fringe scanning imaging is completed, the controller 5 controls an image processor 6 (image generator 6b) to generate X-ray images from a plurality of image signals accumulated in the storage 6a of the image processor 6. Furthermore, the controller 5 controls the image processor 6 (image generator 6b) to reconstruct the generated X-ray images and generate the reconstructed image 11.

The radiation phase contrast imaging device 100 according to the second embodiment of the present invention is configured to operate in a high-speed imaging mode in order to quickly generate the reconstructed image 11. In the high-speed imaging mode, the controller 5 performs control to capture X-ray images with a shorter X-ray charge accumulation time in the X-ray detector 4 than that in a standard imaging mode, and controls the image processor 6 to generate the reconstructed image 11 from the X-ray images acquired with the acquired shorter charge accumulation time. The charge accumulation time refers to a time from when a light receiving element of the X-ray detector 4 receives X-rays until the light receiving element converts the X-rays into image signals.

Figure 5:
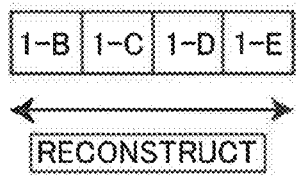
FIG. 5 is a diagram showing the timing of reconstructed image generation in a high-speed imaging mode according to a second embodiment of the present invention.
Figure 5:
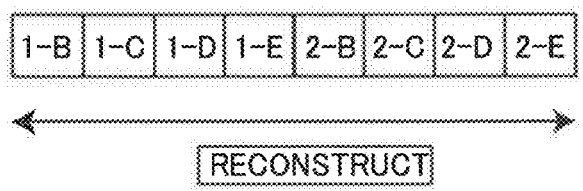
Figure 5:
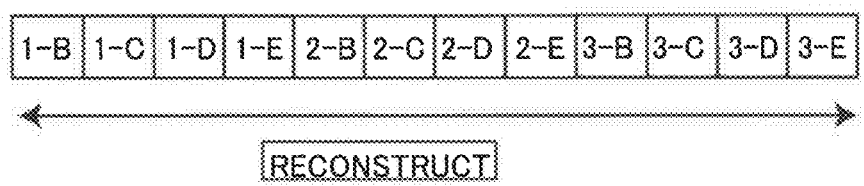
Figure 6:
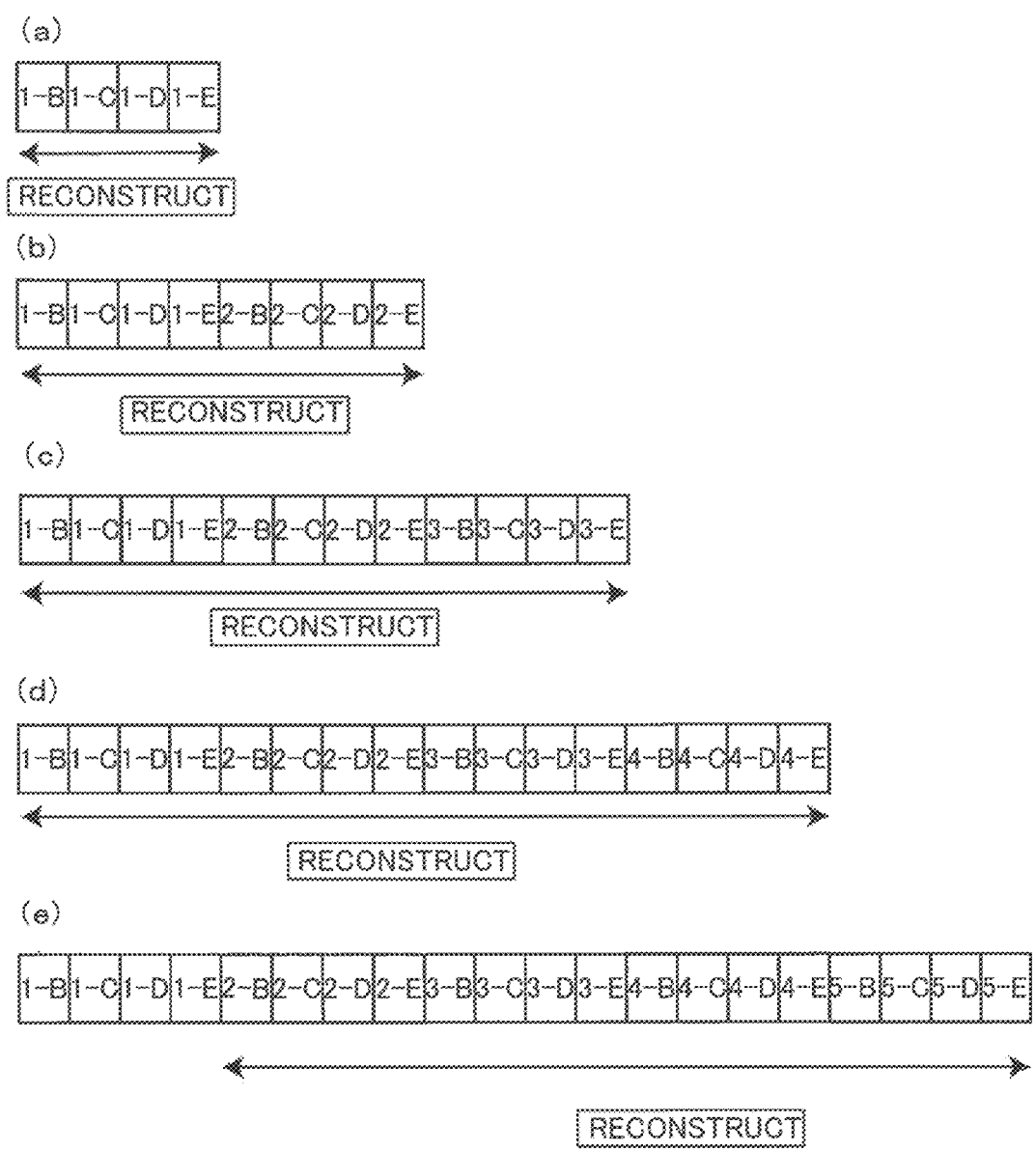
FIG. 6 is a diagram showing the timing of reconstructed image generation in the high-speed imaging mode according to the second embodiment of the present invention.

The operation of the radiation phase contrast imaging device 100 according to the second embodiment of the present invention in the high-speed imaging mode is now described with reference to FIGS. 5 to 7. In FIGS. 5 to 7, each step is represented by a rectangle. A number written in the rectangle represents n-th fringe scanning imaging, and an alphabet represents the position of the grating (see FIG. 4). In one step, the radiation phase contrast imaging device 100 acquires a plurality of X-ray images and accumulates them in the storage 6a of the image processor 6. First, the radiation phase contrast imaging device 100 performs the first fringe scanning imaging from 1-B to 1-E. When the fringe scanning imaging is completed, the controller 5 controls the image processor 6 (image generator 6b) to generate the X-ray images from the plurality of image signals accumulated in the storage 6a of the image processor 6. Furthermore, the controller 5 controls the image processor 6 (image generator 6b) to reconstruct the generated X-ray images and generate the reconstructed image 11. The image processor 6 (image generator 6b) generates the reconstructed image 11 using X-ray images acquired in a total of four steps from 1-B to 1-E (see FIG. 5a).

The radiation phase contrast imaging device 100 performs second fringe scanning imaging from 2-B to 2-E after the first fringe scanning imaging is completed. When the second fringe scanning imaging is completed, the controller 5 controls the image processor 6 (image generator 6b) to generate X-ray images from a plurality of image signals accumulated in the storage 6a of the image processor 6. The controller 5 controls the image generator 6b to reconstruct the generated X-ray images and generate the reconstructed image 11. The image processor 6 (image generator 6b) generates the reconstructed image 11 using X-ray images acquired in a total of eight steps from 1-B to 2-E (see FIG. 5b). Note that when the reconstructed image 11 is created from a plurality of fringe scanning imaging operations, the reconstructed image 11 is generated after adding or averaging is performed for each X-ray image acquired with the same step position.

When the second fringe scanning imaging is completed, the radiation phase contrast imaging device 100 performs third fringe scanning imaging from 3-B to 3-E. When the fringe scanning imaging is completed, the controller 5 controls the image processor 6 (image generator 6b) to generate X-ray images from a plurality of image signals accumulated in the storage 6a of the image processor 6. The controller 5 controls the image processor 6 (image generator 6b) to reconstruct the generated X-ray images and generate the reconstructed image 11. The image processor 6 (image generator 6b) generates the reconstructed image 11 using X-ray images acquired in a total of twelve steps from 1-B to 3-E (see FIG. 5c). Thus, every time the fringe scanning imaging is completed, the image processor 6 (image generator 6b) controls the image processor 6 (image generator 6b) to generate X-ray images from a plurality of image signals accumulated in the storage 6a of the image processor 6. Furthermore, the controller 5 generates the reconstructed image 11 using the generated X-ray images.

In the second embodiment of the present invention, in addition to the above configuration, a user can set a predetermined number of fringe scanning imaging operations used to generate the reconstructed image 11 in the controller 5. When the number of fringe scanning imaging operations is less than the set predetermined number, the controller 5 controls the image processor 6 (image generator 6b) to generate the reconstructed image 11 using a plurality of X-ray images acquired in the previous fringe scanning imaging and a plurality of X-ray images acquired in new fringe scanning imaging. When the number of fringe scanning imaging operations exceeds the set predetermined number, the controller 5 controls the image processor 6 (image generator 6b) to generate the reconstructed image 11 from X-ray images acquired by the predetermined number of most recent fringe scanning imaging operations. At this time, the controller 5 may perform control to delete the X-ray images that are not used for reconstruction from the image processor 6 (storage 6a).

An example in which the predetermined number of fringe scanning imaging operations is four is now described. First, the radiation phase contrast imaging device 100 performs first fringe scanning imaging from 1-B to 1-E. When the fringe scanning imaging is completed, the controller 5 performs control to generate X-ray images from a plurality of image signals accumulated in the storage 6a of the image processor 6. Furthermore, the controller 5 controls the image processor 6 (image generator 6b) to reconstruct the generated X-ray images and generate the reconstructed image 11. The image processor 6 (image generator 6b) generates the reconstructed image 11 using X-ray images acquired in a total of four steps from 1-B to 1-E (see FIG. 6a).

When the first fringe scanning imaging is completed, the radiation phase contrast imaging device 100 performs second fringe scanning imaging from 2-B to 2-E. When the fringe scanning imaging is completed, the controller 5 performs control to generate X-ray images from a plurality of image signals accumulated in the storage 6a of the image processor 6. Furthermore, the controller 5 controls the image processor 6 (image generator 6b) to reconstruct the generated X-ray images and generate the reconstructed image 11. The image processor 6 (image generator 6b) generates the reconstructed image 11 using X-ray images acquired in a total of eight steps from 1-B to 2-E (see FIG. 6b).

When the second fringe scanning imaging is completed, the radiation phase contrast imaging device 100 performs third fringe scanning imaging from 3B to 3E. When the fringe scanning imaging is completed, the controller 5 controls the image processor 6 (image generator 6b) to generate X-ray images from a plurality of image signals accumulated in the storage 6a of the image processor 6. Furthermore, the controller 5 performs control to generate X-ray images. Furthermore, the controller 5 controls the image processor 6 (image generator 6b) to reconstruct the generated X-ray images and generate the reconstructed image 11. The image processor 6 (image generator 6b) generates the reconstructed image 11 using X-ray images acquired in a total of twelve steps from 1-B to 3-E (see FIG. 6c).

When the third fringe scanning imaging is completed, the radiation phase contrast imaging device 100 performs fourth fringe scanning imaging from 4B to 4E. When the fringe scanning imaging is completed, the controller 5 controls the image processor 6 (image generator 6b) to generate X-ray images from a plurality of image signals accumulated in the storage 6a of the image processor 6. Furthermore, the controller 5 controls the image processor 6 (image generator 6b) to reconstruct the generated X-ray images and generate the reconstructed image 11. The image processor 6 (image generator 6b) generates the reconstructed image 11 using X-ray images acquired in a total of sixteen steps from 1-B to 4-E (see FIG. 6d).

When the fourth fringe scanning imaging is completed, the radiation phase contrast imaging device 100 performs fifth fringe scanning imaging from 5-B to 5-E. When the fringe scanning imaging is completed, the controller 5 controls the image processor 6 to acquire X-ray images from the X-ray detector 4 and generate the reconstructed image 11. At this time, the number of fringe scanning imaging operations exceeds the predetermined number, and thus the controller 5 controls the image processor 6 (image generator 6b) to generate the reconstructed image 11 using X-ray images acquired by the four most recent fringe scanning imaging operations. Specifically, the image processor 6 (image generator 6b) generates the reconstructed image 11 using the X-ray images acquired by the second to fifth fringe scanning imaging (X-ray images acquired in a total of sixteen steps from 2-B to 5-E) (see FIG. 6e).

In the second embodiment of the present invention, the user can set a predetermined number of steps in the controller 5. When the number of steps is less than the set predetermined number, the controller 5 controls the image processor 6 to generate the reconstructed image 11 using a plurality of X-ray images acquired in the previous fringe scanning imaging and a plurality of X-ray images acquired in new fringe scanning imaging. When the number of steps exceeds the input number, the controller 5 controls the image processor 6 (image generator 6b) to generate the reconstructed image 11 from X-ray images acquired in the predetermined number of most recent steps. At this time, the controller 5 may control the image processor 6 (storage 6a) to delete the X-ray images acquired by the fringe scanning imaging before the predetermined number of most recent steps, which are not used. An example in which the predetermined number is sixteen is now described. The predetermined number is preferably a multiple of the number of times of fringe scanning imaging.

First, the radiation phase contrast imaging device 100 performs first fringe scanning imaging from 1-B to 1-E. When the fringe scanning imaging is completed, the controller 5 controls the image processor 6 (image generator 6b) to generate X-ray images from a plurality of image signals accumulated in the storage 6a of the image processor 6. Furthermore, the controller 5 controls the image processor 6 to generate the reconstructed image 11 from the generated X-ray images. The image processor 6 generates the reconstructed image 11 using X-ray images acquired in a total of four steps from 1-B to 1-E (see FIG. 7a).

When the first fringe scanning imaging is completed, the radiation phase contrast imaging device 100 performs second fringe scanning imaging from 2-B to 2-E. When the fringe scanning imaging is completed, the controller 5 controls the image processor 6 (image generator 6b) to generate X-ray images from a plurality of image signals accumulated in the storage 6a of the image processor 6. Furthermore, the controller 5 controls the image processor 6

(image generator 6b) to generate the reconstructed image 11 from the generated X-ray images. The image processor 6 (image generator 6b) generates the reconstructed image 11 using X-ray images acquired in a total of eight steps from 1-B to 2-E (see FIG. 7b).

When the second fringe scanning imaging is completed, the radiation phase contrast imaging device 100 performs third fringe scanning imaging from 3-B to 3-E. When the fringe scanning imaging is completed, the controller 5 controls the image processor 6 (image generator 6b) to generate X-ray images from a plurality of image signals accumulated in the storage 6a of the image processor 6. Furthermore, the controller 5 controls the image processor 6 (image generator 6b) to generate the reconstructed image 11 from the generated X-ray images. The image processor 6 (image generator 6b) generates the reconstructed image 11 using X-ray images acquired in a total of twelve steps from 1-B to 3-E (see FIG. 7c).

When the third fringe scanning imaging is completed, the radiation phase contrast imaging device 100 performs fourth fringe scanning imaging from 4-B to 4-E. When the fringe scanning imaging is completed, the controller 5 controls the image processor 6 (image generator 6b) to generate X-ray images from a plurality of image signals accumulated in the storage 6a of the image processor 6. Furthermore, the controller 5 controls the image processor 6 (image generator 6b) to generate the reconstructed image 11 from the generated X-ray images. The image processor 6 (image generator 6b) generates the reconstructed image 11 using X-ray images acquired in a total of sixteen steps from 1-B to 4-E (see FIG. 7d).

When the fourth fringe scanning imaging is completed, the radiation phase contrast imaging device 100 starts fifth fringe scanning imaging. At the end of the fourth fringe scanning imaging, the X-ray images for the sixteen steps are accumulated in the storage 6a of the image processor 6. Consequently, after the fifth fringe scanning imaging, the controller 5 controls the image processor 6 (image generator 6b) to generate the reconstructed image 11 using X-ray images for the sixteen most recent steps every time one step imaging is completed. When a first step (5-B) imaging of the fifth fringe scanning imaging is completed, the controller 5 controls the image processor 6 (image generator 6b) to generate the reconstructed image 11 using X-ray images acquired from a second step of the first fringe scanning imaging to the first step of the fifth fringe scanning imaging (X-ray images acquired in a total of sixteen steps from 1-C to 5-B), which are the sixteen most recent steps. The image processor 6 (image generator 6b) generates the reconstructed image 11 using the X-ray images acquired in a total of four steps from 1-C to 5-B (see FIG. 7e). At this time, the controller 5 may control the image processor 6 (storage 6a) to delete the X-ray images that are not used to generate the reconstructed image 11.

The generated reconstructed image 11 includes an absorption image 11a, a dark-field image 11b, and a phase differential image 11c, for example. The absorption image 11a represents the amount of X-rays transmitted through the subject O. The dark-field image 11b represents the amount of small-angle scattering of X-rays at the subject O. The phase differential image 11c represents an X-ray phase change. The image processor 6 may generate a plurality of reconstructed images 11, and may generate only the dark-field image 11b in which the crack C (defective portion) can be clearly imaged, for example. The generated reconstructed image 11 is displayed on the display 7.

In the second embodiment of the present invention, the radiation phase contrast imaging device 100 may be configured to operate in the standard imaging mode in which X-ray images are captured with a longer X-ray charge accumulation time in the X-ray detector 4 than that in the high-speed imaging mode, and the reconstructed image 11 generated using the acquired X-ray images is displayed on the display 7. A mode switching button may be provided on the display 7 and clicked such that the controller 5 switches between the standard imaging mode and the high-speed imaging mode. In addition, the afterimage suppression effect varies depending on the predetermined number of fringe scanning imaging operations or the predetermined number of steps, and thus the predetermined number of fringe scanning imaging operations or the predetermined number of steps may be automatically increased or decreased depending on the operation speed of a stage 9.

In the high-speed imaging mode in the second embodiment of the present invention, the controller 5 may control the image processor 6 to perform imaging with a smaller number of step movements in the fringe scanning imaging than that in the standard imaging mode.

In the high-speed imaging mode in the second embodiment of the present invention, the controller 5 may control the image processor 6 to perform imaging with a smaller number of captured images per step than that in the standard imaging mode.

In the high-speed imaging mode in the second embodiment of the present invention, the controller 5 may control an X-ray source 1 to reduce the exposure time per X-ray image as compared with the standard imaging mode. The exposure time refers to the time during which the X-ray source 1 radiates X-rays to the subject O, a first grating 2, and the second grating 3 in order to acquire one X-ray image.

Advantages of Second Embodiment

In the second embodiment, the following advantages are obtained.

In the second embodiment of the present invention, the radiation phase contrast imaging device 100 includes the image processor 6 configured to generate the reconstructed image 11 from an X-ray image 10 before reconstruction acquired from the X-ray detector 4, the display 7, and the controller 5 configured or programmed to perform control to display, on the display 7, the X-ray image 10 before reconstruction and the reconstructed image 11 generated by the image processor 6, and is configured to operate in the high-speed imaging mode in which X-ray images are captured with a shorter X-ray charge accumulation time in the X-ray detector 4 than that in the standard imaging mode, and the reconstructed image 11 generated using the acquired X-ray images is displayed on the display 7. Accordingly, the time required to acquire X-ray images necessary for reconstruction can be reduced as compared with the conventional art, and the time required to acquire and display the reconstructed image 11 can be reduced. Thus, the user can quickly grasp the portion to be imaged from the displayed reconstructed image 11. In addition, the user can quickly adjust the position of the subject O and acquire a desired reconstructed image 11.

Furthermore, the image processor 6 is configured to, in the high-speed imaging mode, generate the reconstructed image 11 using the plurality of acquired X-ray images after the first fringe scanning imaging is completed, and generate, in the second and subsequent fringe scanning imaging, the reconstructed image 11 using the plurality of X-ray images acquired in the previous fringe scanning imaging and the plurality of X-ray images acquired in the new fringe scanning imaging. Accordingly, even when the image quality of X-ray images acquired by one fringe scanning imaging operation is rough (a lot of noise), a clearer (less noise) reconstructed image 11 can be acquired as the number of used images is increased by performing the fringe scanning imaging a larger number of times. Consequently, even when X-ray images with a lot of noise and a rough pixel count captured with a shorter X-ray charge accumulation time in the X-ray detector 4 than that in the standard imaging mode are used, a clearer image can be obtained as the number of times of fringe scanning imaging is increased, and the position of the crack C (defective portion) can be quickly grasped. Furthermore, the position of the subject O can be adjusted, and a desired reconstructed image 11 can be acquired.

Furthermore, the image processor 6 is configured to generate the reconstructed image 11 using the X-ray images acquired by the predetermined number of most recent fringe scanning imaging operations in the high-speed imaging mode. Accordingly, as compared with the case in which all the X-ray images acquired by the fringe scanning imaging are used, the number of images used for reconstruction can be reduced, and the time required for reconstruction can be reduced. In addition, it is not necessary to use the images captured before the predetermined number, and thus it is possible to avoid an afterimage remaining when the position of the subject O is moved.

Furthermore, the image processor 6 is configured to generate the reconstructed image 11 using the plurality of X-ray images previously acquired every time one step imaging is completed from predetermined fringe scanning imaging in the high-speed imaging mode. Accordingly, the reconstructed image 11 can be generated and displayed on the display 7 at an even shorter interval than when update is performed every fringe scanning imaging. Consequently, adjustment of the position of the subject O can be reflected in the reconstructed image 11 more quickly.

Furthermore, the reconstructed image 11 includes the absorption image 11a, the dark-field image 11b, and the phase differential image 11c. Accordingly, the user can confirm the portion to be imaged using the absorption image 11a, the dark-field image 11b, and the phase differential image 11c after reconstruction.

Furthermore, the radiation phase contrast imaging device 100 is further configured to operate in the standard imaging mode in which X-ray images are captured with a longer X-ray charge accumulation time in the X-ray detector 4 than that in the high-speed imaging mode, and the reconstructed image 11 generated using the acquired X-ray images is displayed on the display 7, and the controller 5 is configured or programmed to, in the high-speed imaging mode, control the image processor 6 to perform at least one of the following A to C operations: A: to reduce the number of step movements of the fringe scanning imaging as compared with the standard imaging mode, B: to reduce the number of captured images per step as compared with the standard imaging mode, and C: to reduce the exposure time per X-ray image as compared with the standard imaging mode. Accordingly, the time required to acquire X-ray images necessary for reconstruction can be shorter than that in the standard imaging mode. Thus, the time required to acquire and display the reconstructed image 11 can be reduced.

Third Embodiment

Figure 8:
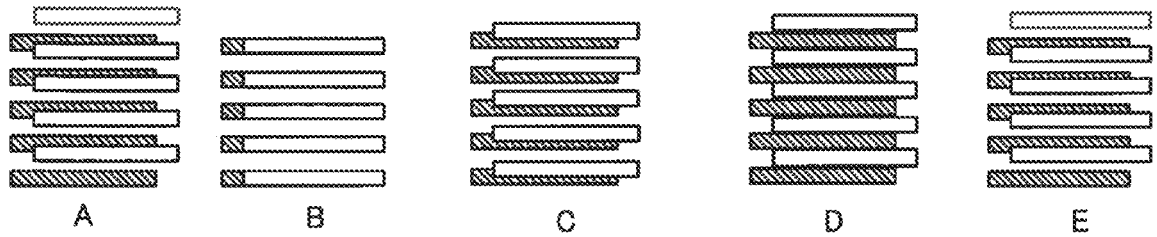
FIG. 8 is a diagram showing grating movement in fringe scanning imaging according to a third embodiment of the present invention.
Figure 8:
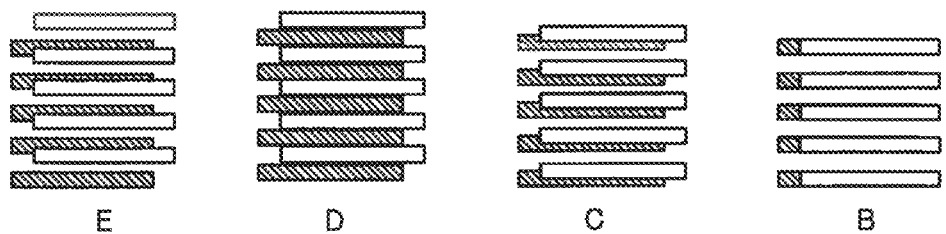

A high-speed imaging mode of a radiation phase contrast imaging device 100 according to a third embodiment of the present invention is now described with reference to FIGS. 8 to 11. Description of the same configuration of the radiation phase contrast imaging device 100 as those of the first embodiment and the second embodiment is omitted. In the third embodiment of the present invention, an example is described in which the radiation phase contrast imaging device 100 is used for non-destructive inspection, and a reconstructed image 11 of a crack C (defective portion) that is a portion to be imaged is generated. The case in which a single fringe scanning imaging operation includes four steps is described below. FIG. 8 shows the positional relationship between a second grating 3 and a self-image viewed as viewed in a Z2 direction when the second grating 3 is imaged at a predetermined pitch in an X direction. A shaded rectangle represents the self-image, and a white rectangle represents the second grating 3.

In the third embodiment of the present invention, the radiation phase contrast imaging device 100 is configured to acquire an image of a subject O by fringe scanning imaging. A moving mechanism 8 switches a direction of step movement of the fringe scanning imaging every time the fringe scanning imaging is completed. In first movement, the moving mechanism 8 moves the second grating 3 to an initial predetermined step position, and arranges the second grating 3 like B. Note that in a first step, the position of the self-image does not need to coincide with the position of the second grating 3. Furthermore, when the second grating 3 is at the initial predetermined step position, it is not necessary to move it. In a state in which the grating is arranged like B, a controller 5 performs imaging of the subject O and controls a storage 6a to accumulate image signals output from an X-ray detector 4. In second movement, the moving mechanism 8 further moves the grating by ¼, and arranges the second grating 3 like C. In a state in which the grating is arranged like C, the controller 5 performs imaging of the subject O and controls the storage 6a to accumulate image signals output from the X-ray detector 4. In third movement, the moving mechanism 8 further moves the grating by ¼, and arranges the second grating 3 like D. In a state in which the grating is arranged like D, the controller 5 performs imaging of the subject O and controls the storage 6a to accumulate image signals output from the X-ray detector 4. In fourth movement, the moving mechanism 8 further moves the grating by ¼, and arranges the second grating 3 like E. In a state in which the grating is arranged like E, the controller 5 performs imaging of the subject O and controls the storage 6a to accumulate image signals output from the X-ray detector 4. Thus, first fringe scanning imaging is completed. Thereafter, the controller 5 controls an image processor 6 (image generator 6b) to generate the reconstructed image 11.

Subsequent to the first fringe scanning imaging, second fringe scanning imaging is performed. In the radiation phase contrast imaging device 100 according to the present invention, in the next fringe scanning imaging, the controller 5 performs imaging of the subject O in a state in which the grating is arranged like E, and controls the storage 6a to accumulate image signals output from the X-ray detector 4. In first movement, the moving mechanism 8 moves the grating by ¼, and arranges the second grating 3 like D. In a state in which the grating is arranged like D, the controller 5 performs imaging of the subject O and controls the storage 6a to accumulate image signals output from the X-ray detector 4. In second movement, the moving mechanism 8 further moves the grating by ¼, and arranges the second grating 3 like C. In a state in which the grating is arranged like C, the controller 5 performs imaging of the subject O and controls the storage 6*a* to accumulate image signals output from the X-ray detector 4. In third movement, the moving mechanism 8 further moves the grating by ¼, and arranges the second grating 3 like B. In a state in which the grating is arranged like B, the controller 5 performs imaging of the subject O and controls the storage 6*a* to accumulate image signals output from the X-ray detector 4. Thus, the second fringe scanning imaging is completed. Thereafter, the controller 5 controls the image processor 6 (image generator 6*b*) to generate the reconstructed image 11. In the next fringe scanning imaging, the controller 5 performs imaging of the subject O in a state in which the second grating 3 is arranged like B, and controls the storage 6*a* to accumulate image signals output from the X-ray detector 4. Thus, fringe scanning imaging is performed without returning to the initial predetermined step position.

Figure 9:
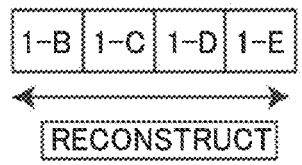
FIG. 9 is a diagram showing the timing of reconstructed image generation in a high-speed imaging mode according to the third embodiment of the present invention.
Figure 9:
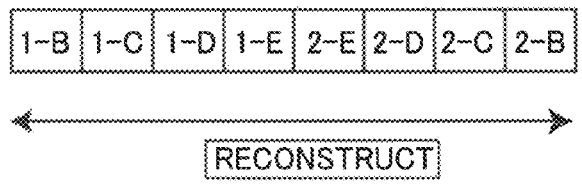
Figure 9:
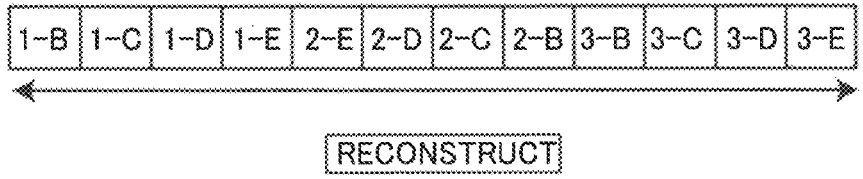
Figure 10:
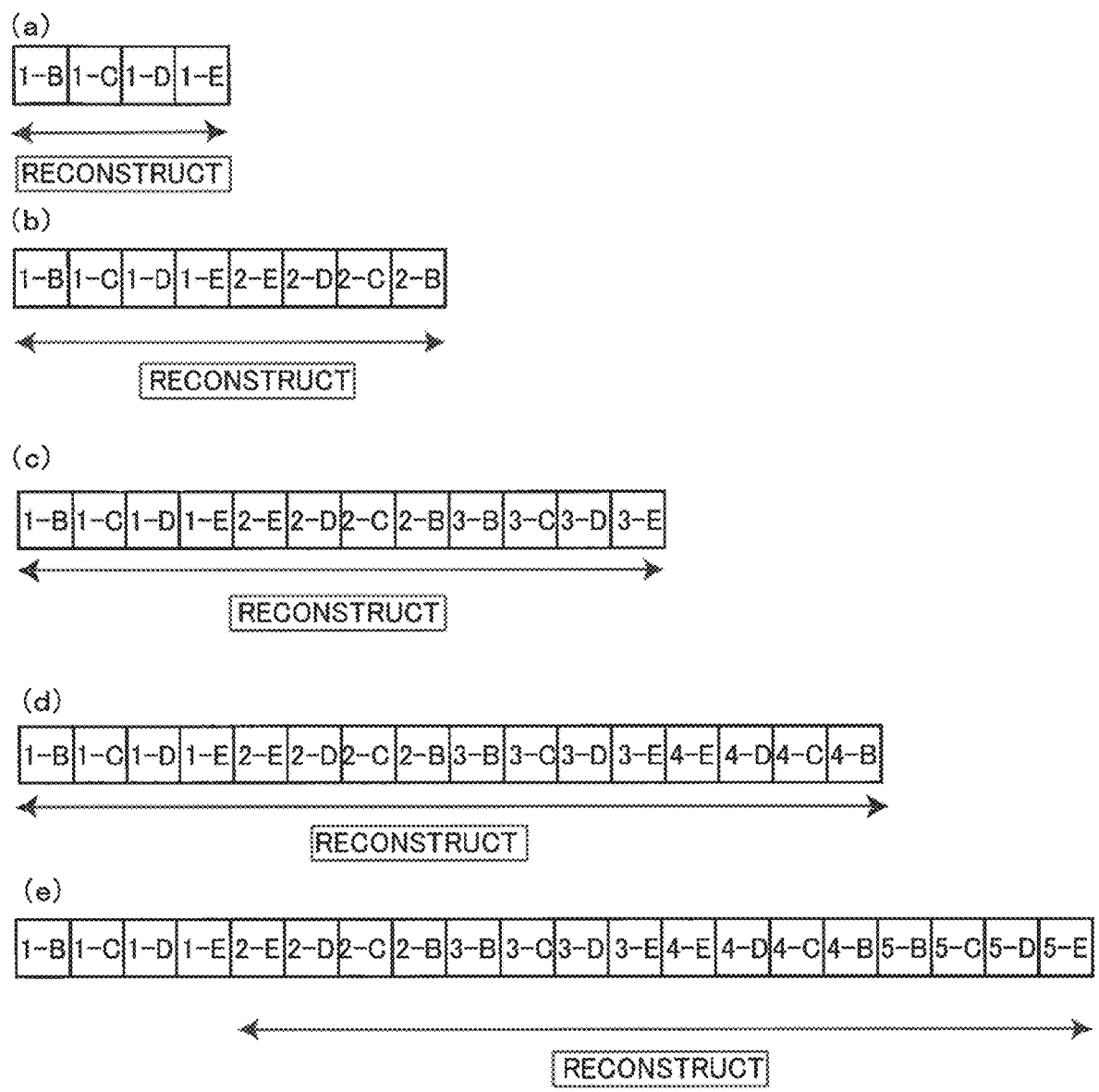
FIG. 10 is a diagram showing the timing of reconstructed image generation in the high-speed imaging mode according to the third embodiment of the present invention.
Figure 11:
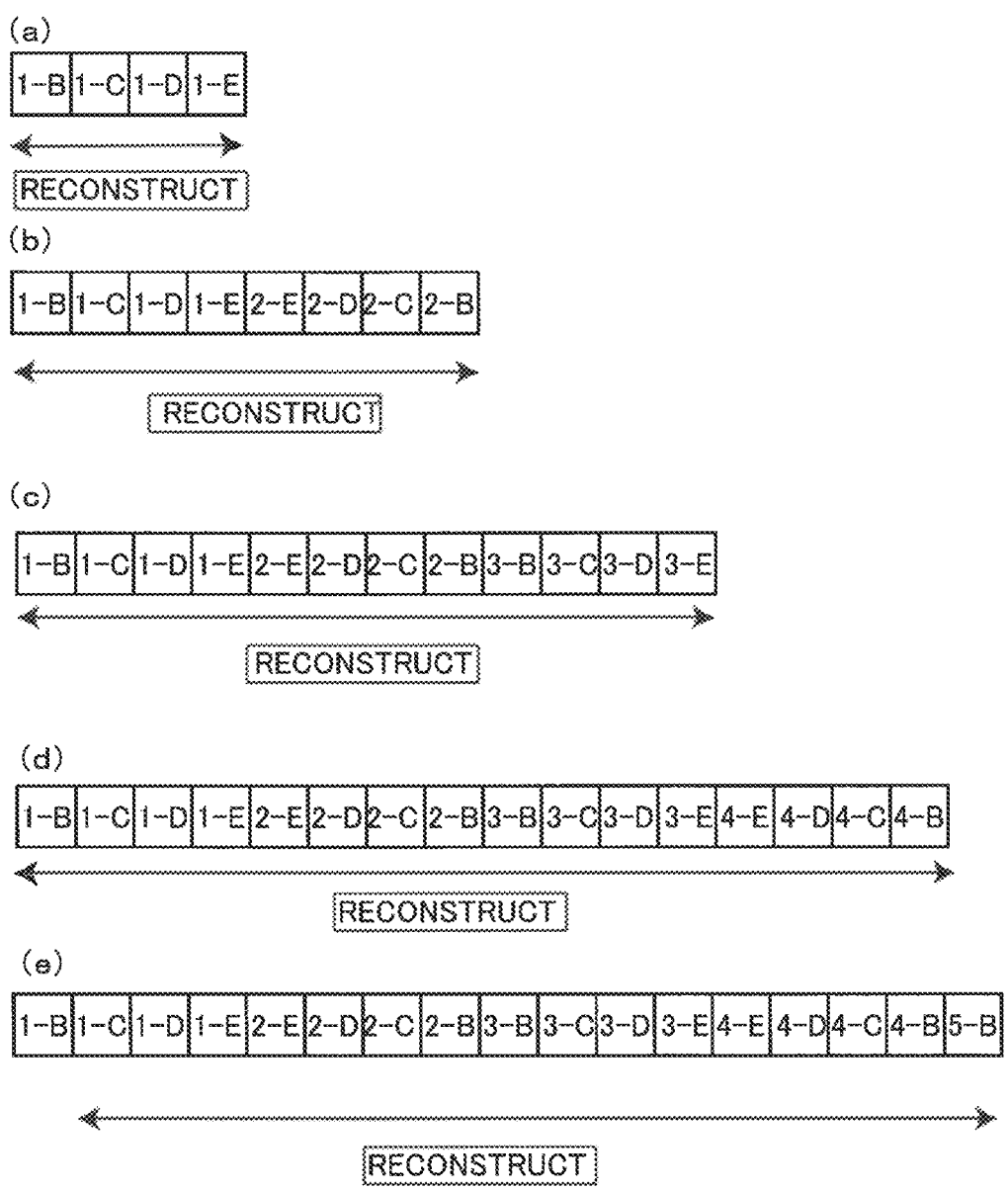
FIG. 11 is a diagram showing the operation of a radiation phase contrast imaging device according to the third embodiment of the present invention.

Next, the operation of the radiation phase contrast imaging device 100 according to the third embodiment of the present invention in the high-speed imaging mode is described. In FIGS. 9 to 11, each step is represented by a rectangle. A number written in the rectangle represents n-th fringe scanning imaging, and an alphabet represents the position of the grating (see FIG. 8). In one step, the radiation phase contrast imaging device 100 acquires a plurality of X-ray images and accumulates them in the storage 6*a* of the image processor 6.

The radiation phase contrast imaging device 100 performs the first fringe scanning imaging from 1-B to 1-E. When the fringe scanning imaging is completed, the controller 5 controls the image processor 6 (image generator 6*b*) to generate X-ray images from a plurality of image signals accumulated in the storage 6*a* of the image processor 6. Furthermore, the controller 5 controls the image processor 6 (image generator 6*b*) to generate the reconstructed image 11 from the generated X-ray images. The image processor 6 generates the reconstructed image 11 using X-ray images acquired in a total of four steps from 1-B to 1-E (see FIG. 9*a*).

When the first fringe scanning imaging is completed, the controller 5 controls the moving mechanism 8 to switch a direction of the fringe scanning imaging. The radiation phase contrast imaging device 100 performs the second fringe scanning imaging from 2-E to 2-B while proceeding in a direction opposite to that of the first fringe scanning imaging. When the fringe scanning imaging is completed, the controller 5 controls the image processor 6 (image generator 6*b*) to generate X-ray images from a plurality of image signals accumulated in the storage 6*a* of the image processor 6. Furthermore, the controller 5 controls the image processor 6 (image generator 6*b*) to generate the reconstructed image 11 from the generated X-ray images. The image processor 6 (image generator 6*b*) generates the reconstructed image 11 using the X-ray images acquired in a total of eight steps from 1-B to 2-B (see FIG. 9*b*).

When the second fringe scanning imaging is completed, the controller 5 controls the moving mechanism 8 to switch a direction of the fringe scanning imaging. The radiation phase contrast imaging device 100 performs third fringe scanning imaging from 3-B to 3-E while moving the second grating 3 in a direction opposite to that of the second fringe scanning imaging. When the fringe scanning imaging is completed, the controller 5 controls the image processor 6 (image generator 6*b*) to generate X-ray images from a plurality of image signals accumulated in the storage 6*a* of the image processor 6. Furthermore, the controller 5 controls the image processor 6 (image generator 6*b*) to generate the reconstructed image 11 from the generated X-ray images. The image processor 6 (image generator 6*b*) generates the reconstructed image 11 using the X-ray images acquired in a total of twelve steps from 1-B to 3-E (see FIG. 9*c*).

Next, an example in which a user sets a predetermined number of fringe scanning imaging operations in the controller 5 is described. An example in which the predetermined number is four is now described.

First, the radiation phase contrast imaging device 100 performs the first fringe scanning imaging from 1-B to 1-E. When the fringe scanning imaging is completed, the controller 5 controls the image processor 6 (image generator 6*b*) to generate the X-ray images from the plurality of image signals accumulated in the storage 6*a* of the image processor 6. Furthermore, the controller 5 controls the image processor 6 (image generator 6*b*) to generate the reconstructed image 11 from the generated X-ray images. The image processor 6 (image generator 6*b*) generates the reconstructed image 11 using the X-ray images acquired in a total of four steps from 1-B to 1-E (see FIG. 10*a*).

When the first fringe scanning imaging is completed, the controller 5 controls the moving mechanism 8 to switch the direction of the fringe scanning imaging. The radiation phase contrast imaging device 100 performs the second fringe scanning imaging from 2-E to 2-B while proceeding in the direction opposite to that of the first fringe scanning imaging. When the fringe scanning imaging is completed, the controller 5 controls the image processor 6 (image generator 6*b*) to generate the X-ray images from the plurality of image signals accumulated in the storage 6*a* of the image processor 6. Furthermore, the controller 5 controls the image processor 6 (image generator 6*b*) to generate the reconstructed image 11 from the generated X-ray images. The image processor 6 (image generator 6*b*) generates the reconstructed image 11 using the X-ray images acquired in a total of eight steps from 1-B to 2-B (see FIG. 10*b*).

When the second fringe scanning imaging is completed, the controller 5 controls the moving mechanism 8 to switch the direction of the fringe scanning imaging. The radiation phase contrast imaging device 100 performs third fringe scanning imaging from 3-B to 3-E while moving the second grating 3 in the direction opposite to that of the second fringe scanning imaging. When the fringe scanning imaging is completed, the controller 5 controls the image processor 6 (image generator 6*b*) to generate X-ray images from a plurality of image signals accumulated in the storage 6*a* of the image processor 6. Furthermore, the controller 5 controls the image processor 6 (image generator 6*b*) to generate the reconstructed image 11 from the generated X-ray images. The image processor 6 (image generator 6*b*) generates the reconstructed image 11 using the X-ray images acquired in a total of twelve steps from 1-B to 3-E (see FIG. 10*c*).

When the third fringe scanning imaging is completed, the controller 5 controls the moving mechanism 8 to switch a direction of the fringe scanning imaging. The radiation phase contrast imaging device 100 performs fourth fringe scanning imaging from 4-E to 4-B while proceeding in a direction opposite to that of the third fringe scanning imaging. When the fringe scanning imaging is completed, the controller 5 controls the image processor 6 (image generator 6*b*) to generate X-ray images from a plurality of image signals accumulated in the storage 6*a* of the image processor 6. Furthermore, the controller 5 controls the image processor 6 (image generator 6*b*) to generate the reconstructed image 11 from the generated X-ray images. The image processor 6 (image generator 6*b*) generates the reconstructed image 11 using the X-ray images acquired in a total of sixteen steps from 1-B to 4-B (see FIG. 10*d*).

When the fourth fringe scanning imaging is completed, the controller 5 controls the moving mechanism 8 to switch a direction of the fringe scanning imaging. The radiation phase contrast imaging device 100 performs fifth fringe scanning imaging from 5-B to 5-E while moving the second grating 3 in a direction opposite to that of the fourth fringe scanning imaging. When the fringe scanning imaging is completed, the controller 5 controls the image processor 6 (image generator 6b) to generate X-ray images from a plurality of image signals accumulated in the storage 6a of the image processor 6. Furthermore, the controller 5 controls the image processor 6 (image generator 6b) to generate the reconstructed image 11 from the generated X-ray images. At this time, the image processor 6 (image generator 6b) generates the reconstructed image 11 using the X-ray images acquired by the second to fifth fringe scanning imaging (X-ray images acquired in a total of sixteen steps from 2-E to 5-E), that is the four most recent fringe scanning imaging operations (see FIG. 10e). At this time, the controller 5 may perform control to delete the X-ray images that are not used for reconstruction from the image processor 6 (storage 6a).

An example in which the user sets a predetermined number of steps in the controller 5 is described with reference to FIG. 11. An example in which the predetermined number is sixteen is now described.

First, the radiation phase contrast imaging device 100 performs the first fringe scanning imaging from 1-B to 1-E. When the fringe scanning imaging is completed, the controller 5 controls the image processor 6 (image generator 6b) to generate the X-ray images from the plurality of image signals accumulated in the storage 6a of the image processor 6. Furthermore, the controller 5 controls the image processor 6 (image generator 6b) to generate the reconstructed image 11 from the generated X-ray images. The image processor 6 (image generator 6b) generates the reconstructed image 11 using the X-ray images acquired in a total of four steps from 1-B to 1-E (see FIG. 11a).

When the first fringe scanning imaging is completed, the controller 5 controls the moving mechanism 8 to switch the direction of the fringe scanning imaging. The radiation phase contrast imaging device 100 performs the second fringe scanning imaging from 2-E to 2-B while moving the second grating 3 in the direction opposite to that of the first fringe scanning imaging. When the fringe scanning imaging is completed, the controller 5 controls the image processor 6 (image generator 6b) to generate the X-ray images from the plurality of image signals accumulated in the storage 6a of the image processor 6. Furthermore, the controller 5 controls the image processor 6 (image generator 6b) to generate the reconstructed image 11 from the generated X-ray images. The image processor 6 (image generator 6b) generates the reconstructed image 11 using the X-ray images acquired in a total of eight steps from 1-B to 2-B (see FIG. 11b).

When the second fringe scanning imaging is completed, the controller 5 controls the moving mechanism 8 to switch the direction of the fringe scanning imaging. The radiation phase contrast imaging device 100 performs the third fringe scanning imaging from 3-B to 3-E while moving the second grating 3 in the direction opposite to the second fringe scanning imaging. When the fringe scanning imaging is completed, the controller 5 controls the image processor 6 (image generator 6b) to generate the X-ray images from the plurality of image signals accumulated in the storage 6a of the image processor 6. Furthermore, the controller 5 controls the image processor 6 (image generator 6b) to generate the reconstructed image 11 from the generated X-ray images. The image processor 6 (image generator 6b) generates the reconstructed image 11 using the X-ray images acquired in a total of twelve steps from 1-B to 3-E (see FIG. 11c).

When the third fringe scanning imaging is completed, the controller 5 controls the moving mechanism 8 to switch the direction of the fringe scanning imaging. The radiation phase contrast imaging device 100 performs the fourth fringe scanning imaging from 4-E to 4-B while moving the second grating 3 in the direction opposite to that of the third fringe scanning imaging. When the fringe scanning imaging is completed, the controller 5 controls the image processor 6 (image generator 6b) to generate the X-ray images from the plurality of image signals accumulated in the storage 6a of the image processor 6. Furthermore, the controller 5 controls the image processor 6 (image generator 6b) to generate the reconstructed image 11 from the generated X-ray images. The image processor 6 (image generator 6b) generates the reconstructed image 11 using the X-ray images acquired in a total of sixteen steps from 1-B to 4-B (see FIG. 11d).

When the fourth fringe scanning imaging is completed, the controller 5 controls the moving mechanism 8 to switch the direction of the fringe scanning imaging. The radiation phase contrast imaging device 100 starts the fifth fringe scanning imaging while moving the second grating 3 in the direction opposite to that of the fourth fringe scanning imaging. At the end of the fourth fringe scanning imaging, the X-ray images for the sixteen steps are accumulated in the storage 6a of the image processor 6. Consequently, after the fifth fringe scanning imaging, the controller 5 controls the image processor 6 to generate the reconstructed image 11 using the X-ray images for the sixteen most recent steps every time one step imaging is completed. When a first step (5-B) imaging is completed, the controller 5 controls the image processor 6 (image generator 6b) to generate X-ray images from a plurality of image signals accumulated in the storage 6a of the image processor 6. Furthermore, the controller 5 controls the image processor 6 (image generator 6b) to generate the reconstructed image 11 from the generated X-ray images. At this time, the image processor 6 (image generator 6b) generates the reconstructed image 11 using X-ray images acquired from a second step of the first fringe scanning imaging to the first step of the fifth fringe scanning imaging (X-ray images acquired in a total of sixteen steps from 1-C to 5-B), which are the sixteen most recent steps (see FIG. 11e). The controller 5 may perform control to delete the X-ray images that are not used for reconstruction from the image processor 6 (storage 6a).

In the third embodiment of the present invention, the generated reconstructed image 11 includes an absorption image 11a, a dark-field image 11b, and a phase differential image 11c, for example. The absorption image 11a represents the amount of X-rays transmitted through the subject O. The dark-field image 11b represents the amount of small-angle scattering of X-rays on a surface of the subject. The phase differential image 11c represents an X-ray phase change. The image processor 6 (image generator 6b) may generate a plurality of reconstructed images 11, and may generate the dark-field image 11b in which the crack C (defective portion) can be clearly imaged, for example. The controller 5 performs control to display the generated reconstructed image 11 on the display 7.

In the third embodiment of the present invention, the radiation phase contrast imaging device 100 may be configured to operate in a standard imaging mode in which X-ray images are captured with a longer X-ray charge accumulation time in the X-ray detector 4 than that in the high-speed imaging mode, and the reconstructed image 11 generated using the acquired X-ray images is displayed on the display 7. A mode switching button may be provided on the display 7 and clicked such that the controller 5 switches between the standard imaging mode and the high-speed imaging mode. In addition, the afterimage suppression effect varies depending on the predetermined number of fringe scanning imaging operations or the predetermined number of steps, and thus the predetermined number of fringe scanning imaging operations or the predetermined number of steps may be automatically increased or decreased depending on the operation speed of a stage 9.

In the high-speed imaging mode, the controller 5 may control the image processor 6 to perform imaging with a smaller number of step movements in the fringe scanning imaging than that in the standard imaging mode.

In the high-speed imaging mode, the controller 5 may control the image processor 6 to perform imaging with a smaller number of captured images per step than that in the standard imaging mode.

In the high-speed imaging mode, the controller 5 may control an X-ray source 1 to reduce the exposure time per X-ray image as compared with the standard imaging mode. The exposure time refers to the time during which the X-ray source 1 radiates X-rays to the subject O, a first grating 2, and the second grating 3 in order to acquire one X-ray image.

Advantages of Third Embodiment

In the third embodiment, the following advantages are obtained.

In the high-speed imaging mode of the radiation phase contrast imaging device 100 according to the third embodiment of the present invention, the moving mechanism 8 is configured to switch the direction of step movement to the opposite direction every time the fringe scanning imaging is completed. Accordingly, the radiation phase contrast imaging device 100 can move to the next fringe scanning imaging in a short time, and the time required to return the position of the grating to the initial predetermined step position can be reduced.

Furthermore, the image processor 6 is configured to generate the reconstructed image 11 using the plurality of acquired X-ray images after the first fringe scanning imaging is completed, and to generate, in the second and subsequent fringe scanning imaging, the reconstructed image 11 using the plurality of X-ray images acquired in the previous fringe scanning imaging and the plurality of X-ray images acquired in the new fringe scanning imaging. Even when the image quality of X-ray images acquired by one fringe scanning imaging operation is rough (a lot of noise), a clearer (less noise) reconstructed image 11 can be acquired as the number of used images is increased by performing the fringe scanning imaging a larger number of times. Consequently, even when X-ray images with a lot of noise and a rough pixel count captured with a shorter X-ray charge accumulation time in the X-ray detector 4 than that in the standard imaging mode are used, a clearer image can be obtained as the number of times of fringe scanning imaging is increased, and the position of the crack C (defective portion) can be quickly grasped. Furthermore, the position of the subject O can be adjusted, and a desired reconstructed image 11 can be acquired.

Furthermore, the image processor 6 is configured to generate the reconstructed image 11 using the X-ray images acquired by the predetermined number of most recent fringe scanning imaging operations. Accordingly, as compared with the case in which all the X-ray images acquired by the fringe scanning imaging are used, the number of images used for reconstruction can be reduced, and the time required for reconstruction can be reduced. In addition, it is not necessary to use the images captured before the predetermined number, and thus it is possible to avoid an afterimage remaining when the position of the subject O is moved.

Furthermore, the image processor 6 is configured to generate the reconstructed image 11 using the plurality of X-ray images previously acquired every time one step imaging is completed from predetermined fringe scanning imaging. Accordingly, the reconstructed image 11 can be generated and displayed on the display 7 at an even shorter interval than when update is performed every fringe scanning imaging. Consequently, adjustment of the position of the subject O can be reflected in the reconstructed image 11 more quickly.

Furthermore, the reconstructed image 11 includes the absorption image 11a, the dark-field image 11b, and the phase differential image 11c. Accordingly, the user can confirm the portion to be imaged using the absorption image 11a, the dark-field image 11b, and the phase differential image 11c after reconstruction.

Furthermore, the radiation phase contrast imaging device 100 is further configured to operate in the standard imaging mode in which X-ray images are captured with a longer X-ray charge accumulation time in the X-ray detector 4 than that in the high-speed imaging mode, and the reconstructed image 11 generated using the acquired X-ray images is displayed on the display 7, and the controller 5 is configured or programmed to, in the high-speed imaging mode, control the image processor 6 to perform at least one of the following A to C operations: A: to reduce the number of step movements of the fringe scanning imaging as compared with the standard imaging mode, B: to reduce the number of captured images per step as compared with the standard imaging mode, and C: to reduce the exposure time per X-ray image as compared with the standard imaging mode. Accordingly, the time required to acquire X-ray images necessary for reconstruction can be shorter than that in the standard mode. Thus, the time required to acquire and display the reconstructed image 11 can be reduced.

MODIFIED EXAMPLES

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

Figure 12:
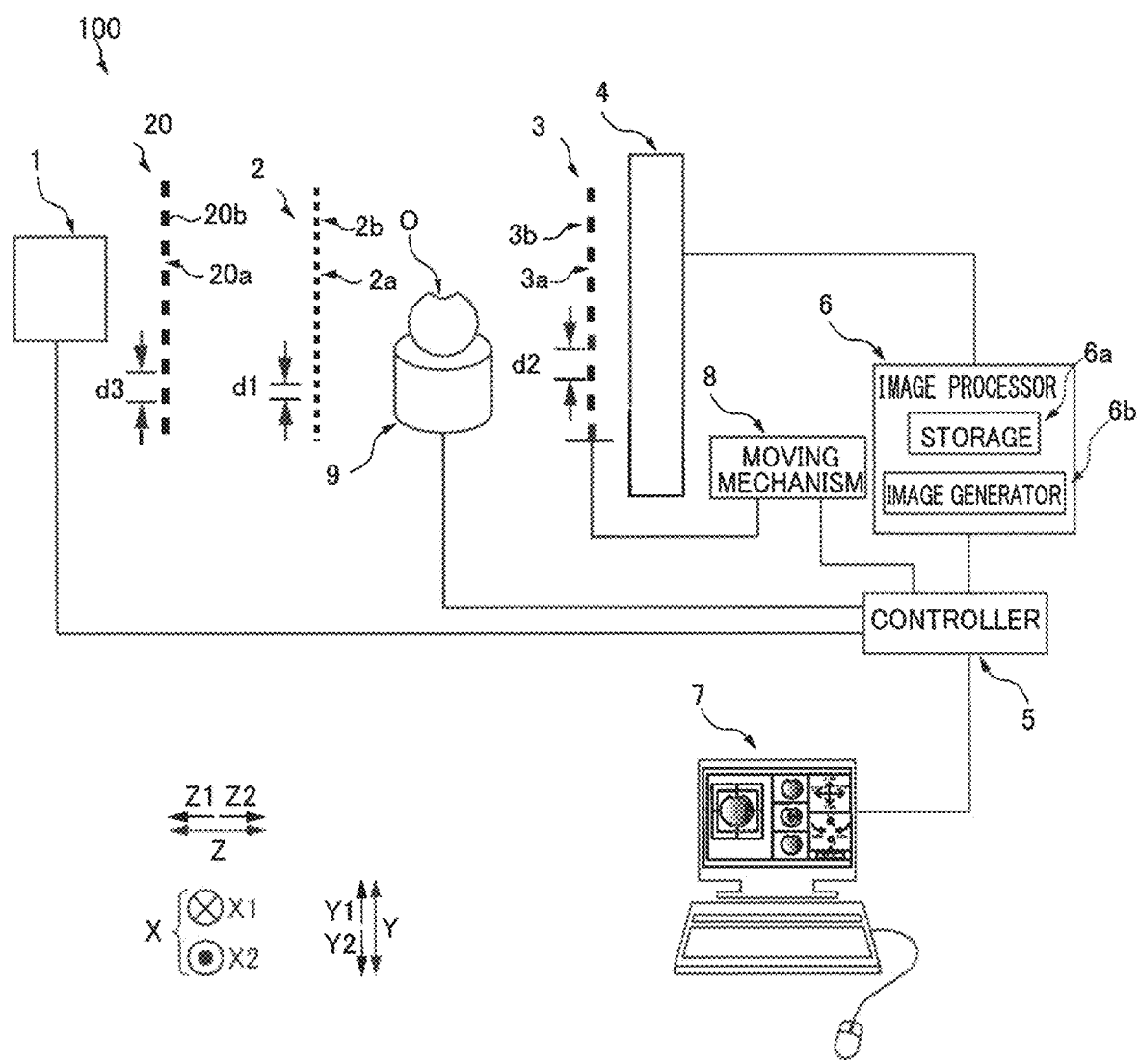
FIG. 12 is a schematic view showing a radiation phase contrast imaging device according to a modified example of the present invention, as viewed in an X direction.

For example, while the example in which the first grating 2 and the second grating 3 are provided as the plurality of gratings has been shown in each of the aforementioned first to third embodiments, the present invention is not limited to this. For example, a third grating 20 may be provided between the X-ray source 1 and the first grating 2 (see FIG. 12). The third grating 20 includes a plurality of slits 20a and X-ray absorbers 20b arranged in a Y direction at a predetermined period (pitch) d3. The slits 20a and the X-ray absorbers 20b are each formed so as to extend linearly. Furthermore, the slits 20a and the X-ray absorbers 20b are each formed so as to extend in parallel. The third grating 20 is arranged between the X-ray source 1 and the first grating 2, and X-rays are radiated thereto from the X-ray source 1. The third grating 20 allows X-rays that have passed through the respective slits 20a to function as linear light sources corresponding to the positions of the respective slits 20a. Thus, the third grating 20 can increase the coherence of the X-rays radiated from the X-ray source 1. Consequently, it is possible to form the self-image of the first grating 2 without depending on the focal diameter of the X-ray source 1, and thus the degree of freedom in selecting the X-ray source 1 can be improved.

While the example in which the mode in which the reconstructed image 11 is acquired is provided separately from the mode in which the X-ray image 10 before reconstruction is acquired has been shown in the aforementioned first embodiment, the present invention is not limited to this. For example, the controller 5 may be configured to generate the reconstructed image 11 while simultaneously controlling the image processor 6 to display the X-ray image 10 before reconstruction on the display 7.

In the aforementioned first embodiment, the display 7 may display data other than the X-ray image 10 before reconstruction, the reconstructed image 11, and the operation panels 14. For example, an image obtained by imaging the subject O with an optical camera may be displayed. Alternatively, positions at which the X-ray image 10 before reconstruction, the reconstructed image 11, the operation panels 14, and the imaging start button 15 are displayed on the display 7 may be changed as appropriate.

In each of the aforementioned first to third embodiments, binning processing may be performed when imaging is performed in the high-speed imaging mode. By doing so, the number of processed pixels can be reduced, and the processing time after imaging can be reduced.

While the example in which the second grating 3 is moved has been shown in each of the aforementioned second and third embodiments, the first grating 2 may be moved.

In each of the aforementioned second and third embodiments, the example in which the number of steps is four in one fringe scanning imaging operation has been described, but the number of steps can be set as appropriate by the user. For example, a clear reconstructed image 11 may be generated by increasing the predetermined number of fringe scanning imaging operations. Alternatively, the reconstructed image 11 may be generated more quickly by reducing the number of steps.

In each of the aforementioned second and third embodiments, the predetermined number of fringe scanning imaging operations is four, but the predetermined number of steps can be set as appropriate by the user. For example, a clear reconstructed image 11 may be generated by increasing the predetermined number of fringe scanning imaging operations. Alternatively, the reconstructed image 11 may be generated more quickly by reducing the number of steps.

In each of the aforementioned second and third embodiments, the predetermined number of steps is sixteen, but the predetermined number of steps can be set as appropriate by the user. For example, a clear reconstructed image 11 may be generated by increasing the predetermined number of fringe scanning imaging operations. Alternatively, the reconstructed image 11 may be generated more quickly by reducing the number of steps.

In each of the aforementioned first to third embodiments, the case in which the radiation phase contrast imaging device 100 is used for non-destructive inspection has been described, but the radiation phase contrast imaging device 100 may be used for medical purposes, for example. In this case, the sizes and shapes of the X-ray source 1, the gratings, the stage 9, etc. and the arrangement of the X-ray source 1, the gratings, the stage 9, etc. can be adjusted as appropriate.

DESCRIPTION OF REFERENCE NUMERALS

1: X-ray source
2: first grating
3: second grating
4: X-ray detector
5: controller
6: image processor
7: display
8: moving mechanism
9: stage
10: X-ray image before reconstruction
11: reconstructed image
14: operation panel
100: radiation phase contrast imaging device
O: subject

The invention claimed is:

1. A radiation phase contrast imaging device comprising:
an X-ray source;
an X-ray detector configured to detect radiated X-rays;
a plurality of gratings including a first grating provided between the X-ray source and the X-ray detector, the first grating through which the X-rays pass, and a second grating irradiated with the X-rays that have passed through the first grating;
a moving mechanism configured to move the first or second grating stepwise;
an image processor configured to generate a reconstructed image from an X-ray image acquired from the X-ray detector;
a display; and
a controller configured or programmed to perform control to display, on the display, the X-ray image before reconstruction and the reconstructed image generated by the image processor.

2. The radiation phase contrast imaging device according to claim 1, wherein the controller is configured or programmed to perform control to display the X-ray image before reconstruction on the display every time one or a plurality of X-ray images are acquired from the X-ray detector, and to control the image processor to generate the reconstructed image and display the reconstructed image that has been generated on the display.

3. The radiation phase contrast imaging device according to claim 1, wherein the controller is configured or programmed to perform control to display the X-ray image before reconstruction and the reconstructed image side by side on the display.

4. The radiation phase contrast imaging device according to claim 1, wherein the reconstructed image includes an absorption image, a dark-field image, and a phase differential image.

5. The radiation phase contrast imaging device according to claim 1, wherein an update period of the X-ray image before reconstruction is shorter than an update period of the reconstructed image.

6. The radiation phase contrast imaging device according to claim 1, wherein the radiation phase contrast imaging device is configured to operate in a high-speed imaging mode in which the X-ray image is captured with a shorter X-ray charge accumulation time in the X-ray detector than that in a standard imaging mode, and the reconstructed image generated using the X-ray image that has been acquired is displayed on the display.

7. The radiation phase contrast imaging device according to claim 6, wherein the reconstructed image includes an absorption image, a dark-field image, and a phase differential image.

8. A radiation phase contrast imaging device comprising:
an X-ray source;
an X-ray detector configured to detect radiated X-rays;
a plurality of gratings including a first grating provided between the X-ray source and the X-ray detector, the first grating through which the X-rays pass, and a second grating irradiated with the X-rays that have passed through the first grating;
a moving mechanism configured to move the first or second grating stepwise;
an image processor configured to generate a reconstructed image from an X-ray image acquired from the X-ray detector;
a display; and
a controller configured or programmed to perform control to display, on the display, the reconstructed image generated by the image processor; wherein the radiation phase contrast imaging device is configured to operate in a high-speed imaging mode in which the X-ray image is captured with a shorter X-ray charge accumulation time in the X-ray detector than that in a standard imaging mode, and the reconstructed image generated using the X-ray image that has been acquired is displayed on the display.

9. The radiation phase contrast imaging device according to claim 8, wherein the image processor is configured to, in the high-speed imaging mode, generate the reconstructed image using a plurality of acquired X-ray images after first fringe scanning imaging is completed, and generate, in second and subsequent fringe scanning imaging, the reconstructed image using a plurality of X-ray images acquired in previous fringe scanning imaging and a plurality of X-ray images acquired in new fringe scanning imaging.

10. The radiation phase contrast imaging device according to claim 9, wherein the image processor is configured to generate the reconstructed image using the X-ray images acquired by a predetermined number of most recent fringe scanning imaging operations in the high-speed imaging mode.

11. The radiation phase contrast imaging device according to claim 9, wherein the image processor is configured to generate the reconstructed image using the plurality of X-ray images previously acquired every time one step imaging is completed from predetermined fringe scanning imaging in the high-speed imaging mode.

12. The radiation phase contrast imaging device according to claim 8, wherein the moving mechanism is configured to switch a direction of step movement to an opposite direction every time fringe scanning imaging is completed in the high-speed imaging mode.

13. The radiation phase contrast imaging device according to claim 8, wherein the radiation phase contrast imaging device is further configured to operate in the standard imaging mode in which the X-ray image is captured with a longer X-ray charge accumulation time in the X-ray detector than that in the high-speed imaging mode, and the reconstructed image generated using the X-ray image that has been acquired is displayed on the display; and
the controller is configured or programmed to, in the high-speed imaging mode, control the image processor to perform at least one of following A to C operations:
A: to reduce a number of step movements of fringe scanning imaging as compared with the standard imaging mode;
B: to reduce a number of captured images per step as compared with the standard imaging mode; and
C: to reduce an exposure time per X-ray image as compared with the standard imaging mode.

\* \* \* \* \*